United States Patent [19]

Guertler et al.

[11] Patent Number: 5,770,427
[45] Date of Patent: Jun. 23, 1998

[54] RETROVIRUS FROM THE HIV GROUP AND ITS USE

[75] Inventors: Lutz G. Guertler, Munich; Josef Eberle, Freising; Albrecht V. Brunn, Augsburg; Stefan Knapp, Marburg-Wehrshausen; Hans-Peter Hauser, Marburg, all of Germany

[73] Assignee: Behring Diagnostics GmbH, Marburg, Germany

[21] Appl. No.: 471,770

[22] Filed: Jun. 6, 1995

Related U.S. Application Data

[62] Division of Ser. No. 132,653, Oct. 5, 1993, abandoned.

[30] Foreign Application Priority Data

Oct. 6, 1992 [DE] Germany ............ 42 33 646.5
Oct. 22, 1992 [DE] Germany ............ 42 35 718.7
Dec. 30, 1992 [DE] Germany ............ 42 44 541.8
Jun. 1, 1993 [DE] Germany ............ 43 18 186.4

[51] Int. Cl.[6] .............. C12N 7/00; C12N 7/04; C12Q 1/70; A61K 39/21
[52] U.S. Cl. ............ 435/235.1; 435/5; 435/236; 424/188.1; 424/208.1; 424/148.1; 424/160.1; 530/388.35; 530/389.4; 536/23.72
[58] Field of Search ................ 424/188.1, 208.1, 424/148.1, 160.1; 435/5, 235.1, 236; 530/388.35, 389.4; 536/23.72

[56] References Cited

PUBLICATIONS

Vanden Haesevelde, et al., (1991) Molecular Cloning and Complete Sequence Analysis of a Highly Divergent African HIV Isolate. Int Conf AIDS.

*Primary Examiner*—Ponnathapura Achutamurthy
*Assistant Examiner*—Hankyel T. Park
*Attorney, Agent, or Firm*—Finnegan, Henderson, Farabow, Garrett & Dunner, L.L.P.

[57] ABSTRACT

A novel immunodeficiency virus is disclosed which has the designation MVP-5180/91 (SEQ ID NO:56) and which has been deposited with the European Collection of Animal Cell Cultures (ECACC) under No. V 920 92 318. The characteristic antigens which can be obtained from it and which can be employed for detecting antibodies against retroviruses which are associated with immunodeficiency diseases are also disclosed, as are the DNA and amino acid sequences of the virus.

2 Claims, 18 Drawing Sheets

SEQUENCE OF MVP-5180

(SEQ. ID NO. 56)

```
   1  CTGGATGGGT TAATTTACTC CCATAAGAGA GCAGAAATCC TGGATCTCTG
  51  GATATATCAC ACTCAGGGAT TCTTCCCTGA TTGGCAGTGT TACACACCGG
 101  GACCAGGACC TAGATTCCCA CTGACATTTG GATGGTTGTT TAAACTGGTA
 151  CCAGTGTCAG CAGAAGAGGC AGAGAGACTG GGTAATACAA ATGAAGATGC
 201  TAGTCTTCTA CATCCAGCTT GTAATCATGG AGCTGAGGAT GCACACGGGG
 251  AGATACTAAA ATGGCAGTTT GATAGATCAT TAGGCTTAAC ACATATAGCC
 301  CTGCAAAAGC ACCCAGAGCT CTTCCCCAAG TAACTGACAC TGCGGGACTT
 351  TCCAGACTGC TGACACTGCG GGACTTTCC AGCGTGGGAG GGATAAGGGG
 401  CGGTTCGGGG AGTGGCTAAC CCTCAGATGC TGCATATAAG CAGCTGCTTT
 451  CCGCTTGTAC CGGGTCTTAG TTAGAGGACC AGGTCTGAGC CCGGGAGCTC
 501  CCTGGCCTCT AGCTGAACCC GCTGCTTAAC GCTCAATAAA GCTTGCCTTG
 551  AGTGAGAAGC AGTGTGTGCT CATCTGTTCA ACCCTGGTGT CTAGAGATCC
 601  CTCAGATCAC TTAGACTGAA GCAGAAAATC TCTAGCAGTG GCGCCCGAAC
 651  AGGGACGCGA AAGTGAAAGT GGAACCAGGG AAGAAAACCT CCGACGCAAC
 701  GGGCTCGGCT TAGCGGAGTG CACCTGCTAA GAGGCGAGAG GAACTCACAA
 751  GAGGGTGAGT AAATTTGCTG GCGGTGGCCA GACCTAGGGG AAGGGCGAAG
 801  TCCCTAGGGG AGGAAGATGG GTGCGAGAGC GTCTGTGTTG ACAGGGAGTA
 851  AATTGGATGC ATGGGAACGA ATTAGGTTAA GGCCAGGATC TAAAAAGGCA
 901  TATAGGCTAA AACATTTAGT ATGGGCAAGC AGGGAGCTGG AAAGATACGC
 951  ATGTAATCCT GGTCTATTAG AAACTGCAGA AGGTACTGAG CAACTGCTAC
1001  AGCAGTTAGA GCCAGCTCTC AAGACAGGGT CAGAGGACCT GAAATCTCTC
1051  TGGAACGCAA TAGCAGTACT CTGGTGCGTT CACAACAGAT TTGACATCCG
1101  AGATACACAG CAGGCAATAC AAAAGTTAAA GGAAGTAATG GCAAGCAGGA
1151  AGTCTGCAGA GGCCGCTAAG GAAGAAACAA GCCCTAGGCA GACAAGTCAA
1201  AATTACCCTA TAGTAACAAA TGCACAGGGA CAAATGGTAC ATCAAGCCAT
```

FIG. 4-1

```
1251  CTCCCCCAGG ACTTTAAATG CATGGGTAAA GGCAGTAGAA GAGAAGGCCT
1301  TTAACCCTGA AATTATTCCT ATGTTTATGG CATTATCAGA AGGGGCTGTC
1351  CCCTATGATA TCAATACCAT GCTGAATGCC ATAGGGGGAC ACCAAGGGGC
1401  TTTACAAGTG TTGAAGGAAG TAATCAATGA GGAAGCAGCA GAATGGGATA
1451  GAACTCATCC ACCAGCAATG GGGCCGTTAC CACCAGGGCA GATAAGGGAA
1501  CCAACAGGAA GTGACATTGC TGGAACAACT AGCACACAGC AAGAGCAAAT
1551  TATATGGACT ACTAGAGGGG CTAACTCTAT CCCAGTAGGA GACATCTATA
1601  GAAAATGGAT AGTGCTAGGA CTAAACAAAA TGGTAAAAAT GTACAGTCCA
1651  GTGAGCATCT TAGATATTAG GCAGGGACCA AAAGAACCAT TCAGAGATTA
1701  TGTAGATCGG TTTTACAAAA CATTAAGAGC TGAGCAAGCT ACTCAAGAAG
1751  TAAAGAATTG GATGACAGAA ACCTTGCTTG TTCAGAATTC AAACCCAGAT
1801  TGTAAACAAA TTCTGAAAGC ATTAGGACCA GAAGCTACTT TAGAAGAAAT
1851  GATGGTAGCC TGTCAAGGAG TAGGAGGGCC AACTCACAAG GCAAAAATAC
1901  TAGCAGAAGC AATGGCTTCT GCCCAGCAAG ATTTAAAGG AGGATACACA
1951  GCAGTATTCA TGCAAAGAGG GCAGAATCCA AATAGAAAAG GGCCCATAAA
2001  ATGCTTCAAT TGTGGAAAAG AGGGACATAT AGCAAAAAAC TGTCGAGCAC
2051  CTAGAAAAAG GGGTTGCTGG AAATGTGGAC AGGAAGGTCA CCAAATGAAA
2101  GATTGCAAAA ATGGAAGACA GGCAAATTTT TTAGGGAAGT ACTGGCCTCC
2151  GGGGGGCACG AGGCCAGGCA ATTATGTGCA GAAACAAGTG TCCCCATCAG
2201  CCCCACCAAT GGAGGAGGCA GTGAAGGAAC AAGAGAATCA GAGTCAGAAG
2251  GGGGATCAGG AAGAGCTGTA CCCATTTGCC TCCCTCAAAT CCCTCTTTGG
2301  GACAGACCAA TAGTCACAGC AAAGGTTGGG GGTCATCTAT GTGAGGCTTT
2351  ACTGGATACA GGGGCAGATG ATACAGTATT AAATAACATA CAATTAGAAG
2401  GAAGATGGAC ACCAAAAATG ATAGGGGGTA TAGGAGGCTT TATAAAAGTA
2451  AAAGAGTATA ACAATGTGAC AGTAGAAGTA CAAGGAAAGG AAGTACAGGG
2501  AACAGTATTG GTGGGACCTA CTCCTGTTAA TATTCTTGGG AGAAACATAT
2551  TGACAGGATT AGGATGTACA CTAAATTTCC CTATAAGTCC CATAGCCCCA
```

FIG. 4-2

2601 GTGCCAGTAA AGCTAAAACC AGGAATGGAT GGACCAAAAG TAAAACAATG
2651 GCCCCTATCT AGAGAGAAAA TAGAAGCACT AACTGCAATA TGTCAAGAAA
2701 TGGAACAGGA AGGAAAAATC TCAAGAATAG GACCTGAAAA TCCTTATAAT
2751 ACACCTATTT TTGCTATAAA AAGAAAGAT AGCACTAAGT GGAGAAAATT
2801 GGTAGACTTC AGAGAATTAA ATAAAGAAC ACAAGATTTC TGGGAGGTGC
2851 AATTAGGTAT TCCACATCCA GGGGGTTTAA AGCAAAGGCA ATCTGTTACA
2901 GTCTTAGATG TAGGAGATGC TTATTTCTCA TGCCCTTTAG ATCCAGACTT
2951 TAGAAAATAC ACTGCCTTCA CTATTCCTAG TGTGAACAAT GAGACCCCAG
3001 GAGTAAGATA CCAGTACAAT GTCCTCCCGC AAGGGTGGAA AGGTTCACCA
3051 GCCATATTTC AGAGTTCAAT GACAAGATT CTAGATCCAT TTAGAAAAG
3101 CAACCCAGAA GTAGAAATTT ATCAGTACAT AGATGACTTA TATGTAGGAT
3151 CAGATTTACC ATTGGCAGAA CATAGAAAGA GGGTCGAATT GCTTAGGGAA
3201 CATTTATATC AGTGGGGATT TACTACCCCT GATAAAAAGC ATCAGAAGGA
3251 ACCTCCCTTT TTATGGATGG GATATGAGCT CCACCCAGAC AAGTGGACAG
3301 TACAGCCCAT CCAATTGCCT GACAAGAAG TGTGGACAGT AAATGATATA
3351 CAAAAATTAG TAGGAAAATT AAATTGGGCA AGTCAAATCT ATCAAGGAAT
3401 TAGAGTAAAA GAATTGTGCA AGTTAATCAG AGGAACCAAA TCATTGACAG
3451 AGGTAGTACC TTTAAGTAAA GAGGCAGAAC TAGAATTAGA AGAAAACAGA
3501 GAAAAGCTAA AAGAGCCAGT ACATGGAGTA TATTACCAGC CTGACAAAGA
3551 CTTGTGGGTT AGTATTCAGA AGCATGGAGA AGGGCAATGG ACTTACCAGG
3601 TATATCAGGA TGAACATAAG AACCTTAAAA CAGGAAAATA TGCTAGGCAA
3651 AAGGCCTCCC ACACAAATGA TATAAGACAA TTGGCAGAAG TAGTCCAGAA
3701 GGTGTCTCAA GAAGCTATAG TTATATGGGG GAAATTACCT AAATTCAGGC
3751 TGCCAGTTAC TAGAGAAACT TGGGAAACTT GGTGGGCAGA ATATTGGCAG
3801 GCCACCTGGA TTCCTGAATG GGAATTTGTC AGCACACCCC CATTGATCAA
3851 ATTATGGTAC CAGTTAGAAA CAGAACCTAT TGTAGGGGCA GAAACCTTTT
3901 ATGTAGATGG AGCAGCTAAT AGGAATACAA AACTAGGAAA GGCGGGATAT

*FIG. 4-3*

3951 GTTACAGAAC AAGGAAAACA GAACATAATA AAGTTAGAAG AGACAACCAA
4001 TCAAAAGGCT GAATTAATGG CTGTATTAAT AGCCTTGCAG GATTCCAAGG
4051 AGCAAGTAAA CATAGTAACA GACTCACAAT ATGTATTGGG CATCATATCC
4101 TCCCAACCAA CACAGAGTGA CTCCCTATA GTTCAGCAGA TAATAGAGGA
4151 ACTAACAAAA AAGGAACGAG TGTATCTTAC ATGGGTTCCT GCTCACAAAG
4201 GCATAGGAGG AAATGAAAAA ATAGATAAAT TAGTAAGCAA AGACATTAGA
4251 AGAGTCCTGT TCCTGGAAGG AATAGATCAG GCACAAGAAG ATCATGAAAA
4301 ATATCATAGT AATTGGAGAG CATTAGCTAG TGACTTTGGA TTACCACCAA
4351 TAGTAGCCAA GGAAATCATT GCTAGTTGTC CTAAATGCCA TATAAAGGG
4401 GAAGCAACGC ATGGTCAAGT AGACTACAGC CCAGAGATAT GGCAAATGGA
4451 TTGTACACAT TTAGAAGGCA AAATCATAAT AGTTGCTGTC CATGTAGCAA
4501 GTGACTTTAT AGAAGCAGAG GTGATACCAG CAGAAACAGG ACAGGAAACT
4551 GCCTATTTCC TGTTAAAATT AGCAGCAAGA TGGCCTGTCA AAGTAATACA
4601 TACAGACAAT GGACCTAATT TTACAAGTGC AGCCATGAAA GCTGCATGTT
4651 GGTGGACAGG CATACAACAT GAGTTTGGGA TACCATATAA TCCACAAAGT
4701 CAAGGAGTAG TAGAAGCCAT GAATAAAGAA TTAAAATCTA TTATACAGCA
4751 GGTGAGGGAC CAAGCAGAGC ATTTAAAAAC AGCAGTACAA ATGGCAGTCT
4801 TTGTTCACAA TTTTAAAAGA AAAGGGGGGA TTGGGGGGTA CACTGCAGGG
4851 GAGAGACTAA TAGACATACT AGCATCACAA ATACAAACAA CAGAACTACA
4901 AAAACAAATT TTAAAAATCA ACAATTTTCG GGTCTATTAC AGAGATAGCA
4951 GAGACCCTAT TTGGAAAGGA CCGGCACAAC TCCTGTGGAA AGGTGAGGGG
5001 GCAGTAGTCA TACAAGATAA AGGAGACATT AAAGTGGTAC CAAGAAGAAA
5051 GGCAAAAATA ATCAGAGATT ATGGAAAACA GATGGCAGGT ACTGATAGTA
5101 TGGCAAATAG ACAGACAGAA AGTGAAAGCA TGGAACAGCC TGGTGAAATA
5151 CCATAAATAC ATGTCTAAGA AGGCCGCGAA CTGGCGTTAT AGGCATCATT
5201 ATGAATCCAG GAATCCAAAA GTCAGTTCGG CGGTGTATAT TCCAGTAGCA
5251 GAAGCTGATA TAGTGGTCAC CACATATTGG GGATTAATGC CAGGGGAAAG

FIG. 4-4

5301 AGAGGAACAC TTGGGACATG GGGTTAGTAT AGAATGGCAA TACAAGGAGT
5351 ATAAAACACA GATTGATCCT GAAACAGCAG ACAGGATGAT ACATCTGCAT
5401 TATTTCACAT GTTTTACAGA ATCAGCAATC AGGAAGGCCA TTCTAGGGCA
5451 GAGAGTGCTG ACCAAGTGTG AATACCTGGC AGGACATAGT CAGGTAGGGA
5501 CACTACAATT CTTAGCCTTG AAAGCAGTAG TGAAAGTAAA AAGAAATAAG
5551 CCTCCCCTAC CCAGTGTCCA GAGATTAACA GAAGATAGAT GGAACAAGCC
5601 CTGGAAAATC AGGGACCAGC TAGGGAGCCA TTCAATGAAT GGACACTAGA
5651 GCTCCTGGAA GAGCTGAAAG AAGAAGCAGT AAGACATTTC CCTAGGCCTT
5701 GGTTACAAGC CTGTGGGCAG TACATTTATG AGACTTATGG AGACACTTGG
5751 GAAGGAGTTA TGGCAATTAT AAGAATCTTA CAACAACTAC TGTTTACCCA
5801 TTATAGAATT GGATGCCAAC ATAGTAGAAT AGGAATTCTC CCATCTAACA
5851 CAAGAGGAAG AGGAAGAAGA AATGGATCCA GTAGATCCTG AGATGCCCCC
5901 TTGGCATCAC CCTGGGAGCA AGCCCCAAAC CCCTTGTAAT AATTGCTATT
5951 GCAAAGATG CTGCTATCAT TGCTATGTTT GTTTCACAAA GAAGGGTTTG
6001 GGAATCTCCC ATGGCAGGAA GAAGCGAAGA AGACCAGCAG CTGCTGCAAG
6051 CTATCCAGAT AATAAAGATC CTGTACCAGA GCAGTAAGTA ACGCTGATGC
6101 ATCAAGAGAA CCTGCTAGCC TTAATAGCTT TAAGTGCTTT GTGTCTTATA
6151 AATGTACTTA TATGGTTGTT TAACCTTAGA ATTTATTTAG TGCAAAGAAA
6201 ACAAGATAGA AGGGAGCAGG AAATACTTGA AGATTAAGG AGAATAAAGG
6251 AAATCAGGGA TGACAGTGAC TATGAAAGTA ATGAAGAAGA ACAACAGGAA
6301 GTCATGGAGC TTATACATAG CCATGGCTTT GCTAATCCCA TGTTTGAGTT
6351 ATAGTAAACA ATTGTATGCC ACAGTTTATT CTGGGGTACC TGTATGGGAA
6401 GAGGCAGCAC CAGTACTATT CTGTGCTTCA GATGCTAACC TAACAAGCAC
6451 TGAACAGCAT AATATTTGGG CATCACAAGC CTGCGTTCCT ACAGATCCCA
6501 ATCCACATGA ATTTCCACTA GGCAATGTGA CAGATAACTT TGATATATGG
6551 AAAAATTACA TGGTGGACCA AATGCATGAA GACATCATTA GTTTGTGGGA
6601 ACAGAGTTTA AAGCCTTGTG AGAAAATGAC TTTCTTATGT GTACAAATGA

FIG. 4-5

6651 ACTGTGTAGA TCTGCAAACA AATAAAACAG GCCTATTAAA TGAGACAATA
6701 AATGAGATGA GAAATTGTAG TTTTAATGTA ACTACAGTCC TCACAGACAA
6751 AAAGGAGCAA AAACAGGCTC TATTCTATGT ATCAGATCTG AGTAAGGTTA
6801 ATGACTCAAA TGCAGTAAAT GGAACAACAT ATATGTTAAC TAATTGTAAC
6851 TCCACAATTA TCAAGCAGGC CTGTCCGAAG GTAAGTTTTG AGCCCATTCC
6901 CATACACTAT TGTGCTCCAA CAGGATATGC CATCTTTAAG TGTAATGACA
6951 CAGACTTTAA TGGAACAGGC CTATGCCACA ATATTTCAGT GGTTACTTGT
7001 ACACATGGCA TCAAGCCAAC AGTAAGTACT CAACTAATAC TGAATGGGAC
7051 ACTCTCTAGA GAAAAGATAA GAATTATGGG AAAAAATATT ACAGAATCAG
7101 CAAAGAATAT CATAGTAACC CTAAACACTC CTATAAACAT GACCTGCATA
7151 AGAGAAGGAA TTGCAGAGGT ACAAGATATA TATACAGGTC CAATGAGATG
7201 GCGCAGTATG ACACTTAAAA GAAGTAACAA TACATCACCA AGATCAAGGG
7251 TAGCTTATTG TACATATAAT AAGACTGTAT GGGAAAATGC CCTACAACAA
7301 ACAGCTATAA GGTATTTAAA TCTTGTAAAC CAAACAGAGA ATGTTACCAT
7351 AATATTCAGC AGAACTAGTG GTGGAGATGC AGAAGTAAGC CATTTACATT
7401 TTAACTGTCA TGGAGAATTC TTTTATTGTA ACACATCTGG GATGTTTAAC
7451 TATACTTTTA TCAACTGTAC AAAGTCCGGA TGCCAGGAGA TCAAAGGGAG
7501 CAATGAGACC AATAAAAATG GTACTATACC TTGCAAGTTA AGACAGCTAG
7551 TAAGATCATG GATGAAGGGA GAGTCGAGAA TCTATGCACC TCCCATCCCC
7601 GGCAACTTAA CATGTCATTC AACATAACT GGAATGATTC TACAGTTAGA
7651 TCAACCATGG AATTCCACAG GTGAAAATAC ACTTAGACCA GTAGGGGGAG
7701 ATATGAAAGA TATATGGAGA ACTAAATTGT ACAACTACAA AGTAGTACAG
7751 ATAAAACCTT TTAGTGTAGC ACCTACAAAA ATGTCAAGAC CAATAATAAA
7801 CATTCACACC CCTCACAGGG AAAAAGAGC AGTAGGATTG GAATGCTAT
7851 TCTTGGGGGT GCTAAGTGCA GCAGGTAGCA CTATGGGCGC AGCGGCAACA
7901 GCGCTGACGG TACGGACCCA CAGTGTACTG AAGGGTATAG TGCAACAGCA
7951 GGACAACCTG CTGAGAGCGA TACAGGCCCA GCAACACTTG CTGAGGTTAT

*FIG. 4-6*

```
8001  CTGTATGGGG TATTAGACAA CTCCGAGCTC GCCTGCAAGC CTTAGAAACC
8051  CTTATACAGA ATCAGCAACG CCTAAACCTA TGGGGCTGTA AAGGAAAACT
8101  AATCTGTTAC ACATCAGTAA AATGGAACAC ATCATGGTCA GGAAGATATA
8151  ATGATGACAG TATTTGGGAC AACCTTACAT GGCAGCAATG GGACCAACAC
8201  ATAAACAATG TAAGCTCCAT TATATATGAT GAAATACAAG CAGCACAAGA
8251  CCAACAGGAA AAGAATGTAA AAGCATTGTT GGAGCTAGAT GAATGGGCCT
8301  CTCTTTGGAA TTGGTTTGAC ATAACTAAAT GGTTGTGGTA TATAAAATA
8351  GCTATAATCA TAGTGGGAGC ACTAATAGGT ATAAGAGTTA TTATGATAAT
8401  ACTTAATCTA GTGAAGAACA TTAGGCAGGG ATATCAACCC CTCTCGTTGC
8451  AGATCCCTGT CCCACACCGG CAGGAAGCAG AAACGCCAGG AAGAACAGGA
8501  GAAGAAGGTG GAGAAGGAGA CAGGCCCAAG TGGACAGCCT TGCCACCAGG
8551  ATTCTTGCAA CAGTTGTACA CGGATCTCAG GACAATAATC TTGTGGACTT
8601  ACCACCTCTT GAGCAACTTA ATATCAGGGA TCCGGAGGCT GATCGACTAC
8651  CTGGGACTGG GACTGTGGAT CCTGGGACAA AAGACAATTG AAGCTTGTAG
8701  ACTTTGTGGA GCTGTAATGC AATATTGGCT ACAAGAATTG AAAAATAGTG
8751  CTACAAACCT GCTTGATACT ATTGCAGTGT CAGTTGCCAA TTGGACTGAC
8801  GGCATCATCT TAGGTCTACA AAGAATAGGA CAAGGATTCC TTCACATCCC
8851  AAGAAGAATT AGACAAGGTG CAGAAAGAAT CTTAGTGTAA CATGGGGAAT
8901  GCATGGAGCA AAAGCAAATT TGCAGGATGG TCAGAAGTAA GAGATAGAAT
8951  GAGACGATCC TCCTCTGATC CTCAACAACC ATGTGCACCT GGAGTAGGAG
9001  CTGTCTCCAG GGAGTTAGCA ACTAGAGGGG AATATCAAG TTCCCACACT
9051  CCTCAAAACA ATGCAGCCCT TGCATTCCTA GACAGCCACA AAGATGAGGA
9101  TGTAGGCTTC CCAGTAAGAC CTCAAGTGCC TCTAAGGCCA ATGACCTTTA
9151  AAGCAGCCTT TGACCTCAGC TTCTTTTTAA AAGAAAAGGG AGGACTGGAT
9201  GGGTTAATTT ACTCCCATAA GAGAGCAGAA ATCCTGGATC TCTGGATATA
9251  TCACACTCAG GGATTCTTCC CTGATTGGCA GTGTTACACA CCGGGACCAG
9301  GACCTAGATT CCCACTGACA TTTGGATGGT TGTTTAAACT GGTACCAGTG
```

FIG. 4-7

```
9351  TCAGCAGAAG AGGCAGAGAG ACTGGGTAAT ACAAATGAAG ATGCTAGTCT
9401  TCTACATCCA GCTTGTAATC ATGGAGCTGA GGATGCACAC GGGGAGATAC
9451  TAAAATGGCA GTTTGATAGA TCATTAGGCT TAACACATAT AGCCCTGCAA
9501  AAGCACCCAG AGCTCTTCCC CAAGTAACTG ACACTGCGGG ACTTTCCAGA
9551  CTGCTGACAC TGCGGGGACT TTCCAGCGTG GGAGGGATAA GGGGCGGTTC
9601  GGGGAGTGGC TAACCCTCAG ATGCTGCATA TAAGCAGCTG CTTTCCGCTT
9651  GTACCGGGTC TTAGTTAGAG GACCAGGTCT GAGCCCGGGA GCTCCCTGGC
9701  CTCTAGCTGA ACCCGCTGCT TAACGCTCAA TAAAGCTTGC CTTGAGTGAG
9751  AAGCAGTGTG TGCTCATCTG TTCAACCCTG GTGTCTAGAG ATC
```

*FIG. 4-8*

(SEQUENCE ID NO. 57 + 58)

MvP5180

```
 685 AAACCTCCGACGCAACGGGCTCGGCTTAGCGGAGTGCACCTGCTAAGAGG  734
     ||||||||  ||||||||||||||||||||||||||||||||||||||||
   1 aaacctccaacgcaacgggctcggcttagcggagtgcacctgctaagagg   50

735 CGAGAGGAACTCACAAGAGGGTGAGTAAATTTGCTGGCGGTGGCCAGACC  784
     ||||||||||||||||||||||||||||||||||||||||||||||||||
  51 cgagaggaactcacaagagggtgagtaaatttgctggcggtggccagacc  100

785 TAGGGGAAGGGCGAAGTCCCTAGGGGAGGAAGATGGGTGCGAGAGCGTCT  834
     |||||||||||||||||||||||||||||||||||||||||||||  |||
 101 taggggaagggcgaagtccctaggggaggaagatgggtgcgagacggtct  150

835 GTGTTGACAGGGAGTAAATTGGATGCATGGGAACGAATTAGGTTAAGGCC  884
     ||||||||||||||||||||||||||||||||||||||||||||||||||
 151 gtgttgacagggagtaaattggatgcatgggaacgaattaggttaaggcc  200

885 AGGATCTAAAAAGGCATATAGGCTAAAACATTTAGTATGGGCAAGCAGGG  934
     |||||||||||||||||||||||||||| |||||||||||||||||||||
 201 aggatctaaaaaggcatataggctaaaAcatttagtatgggcaagcaggg  200

935 AGCTGGAAAGATACGCATGTAATCCTGGTCTATTAGAAACTGCAGAAGGT  984
     |||||||||||||||||| |||||||||| ||||||||||||||||||||
 251 agctggaaagatacgcatataatcctggtctactagaaactgcagaaggt  300

985 ACTGAGCAACTGCTACAGCAGTTAGAGCCAGCTCTCAAGACAGGGTCAGA  1034
     ||||| ||||||||||||||||||||||||||||||||||||||||||||
 301 actgaacaactgctacagcagttagagccagctctcaagacagggtcaga  350

1035 GGACCTGAAATCTCTCTGGAACGCAATAGCAGTACTCTGGTGCGTTCACA  1084
     |||||||||||  |||||||||||||||||||||||||||||||||||||
 351 ggacctgaaatccctctggaacgcaatagcagtactctggtgcgttcaca  400

1085 ACAGATTTGACATCCGAGATACACAGCAGGCAATACAAAAGTTAAAGGAA  1134
     ||||||||||||||||||||||||||||||||||||||||||||||||||
 401 acagatttgacatccgagatacacagcaggcaatacaaaagttaaaggaa  450

1135 GTAATGGCAAGCAGGAAGTCTGCAGAGGCCGCTAAGGAAGAAACAAGCCC  1184
     |||||||||||||||||||||||||||||||||||||||||||||||| |
 451 gtaatggcaagcaggaagtctgcagaggccgctaaggaagaaacaagctc  500
```

FIG.6-1

```
1185  TAGGCAGACAAGTCAAAATTACCCTATAGTAACAAATGCACAGGGACAAA  1234
      ||||||  ||||||||||||||||||||||||||||||||||||||||||
 501  aaggcaggcaagtcaaaattaccctatagtaacaaatgcacagggacaaa   550

1235  TGGTACATCAAGCCATCTCCCCCAGGACTTTAAATGCATGGGTAAAGGCA  1284
      |||||||||||||||| |||||  ||||||||||||||||||||||||||
 551  tggtacatcaagccatatcccctaggactttaaatgcatgggtaaaggca   600

1285  GTAGAAGAGAAGGCCTTTAACCCTGAAATTATTCCTATGTTTATGGCATT  1334
      ||||||||  ||||||||||||||||||||||||||||||||||||||||
 601  gtagaagaaaaggcctttaaccctgaaattattcctatgtttatggcatt   650

1335  ATCAGAAGGGGCTGTCCCCTATGATATCAATACCATGCTGAATGCCATAG  1384
      ||||||||||||||||||||||||||||||||||||||||||||||||||
 651  atcagaaggggctgtcccctatgatatcaataccatgctgaatgccatag   700

1385  GGGGACACCAAGGGGCTTTACAAGTGTTGAAGGAAGTAATCAATGAGGAA  1434
      ||||||||||||||||||||||||||||||||||||||||||||||||||
 701  ggggacaccaaggggctttacaagtgttgaaggaagtaatcaatgaggaa   750

1435  GCAGCAGAATGGGATAGAACTCATCCACCAGCAATGGGGCCGTTACCACC  1484
      ||||||||  ||||||||||||||||||||||||||||||||||||||||
 751  gcagcagattgggatagaactcatccaccagcaatggggccgttaccacc   800

1485  AGGGCAGATAAGGGAACCAACAGGAAGTGACATTGCTGGAACAACTAGCA  1534
      ||||||||||||||||||||||||||||||||||||||||||||||||||
 801  agggcagataagggaaccaacaggaagtgacattgctggaacaactagca   850

1535  CACAGCAAGAGCAAATTATATGGACTACTAGAGGGGCTAACTCTATCCCA  1584
      ||||||||||||||||||||||||||||||||||||||||||||||||||
 851  cacagcaagagcaaattatatggactactagaggggctaactctatccca   900

1585  GTAGGAGACATCTATAGAAAATGGATAGTGCTAGGACTAAACAAAATGGT  1634
      |||||||||||||||||||||||||||| ||||||||||||||||||||
 901  gtaggagacatctatagaaaatggatagtgttaggactaaacaaaatggt   950

1635  AAAAATGTACAGTCCAGTGAGCATCTTAGATATTAGGCAGGGACCAAAAG  1684
      ||||||||||||||||||||||||||||||||||||||||||||||||||
 951  aaaaatgtacagtccagtgagcatcttagatattaggcagggaccaaaag  1000
```

FIG. 6-2

1685 AACCATTCAGAGATTATGTAGATCGGTTTTACAAAACATTAAGAGCTGAG 1734
1001 aaccattcagagattatgtagatcggttttacaaaacattaagagctgag 1050

1735 CAAGCTACTCAAGAAGTAAAGAATTGGATGACAGAAACCTTGCTTGTTCA 1784
1051 caagctactcaagaagtaaagaattggatgacagaaaccctcgttgttca 1100

1785 GAATTCAAACCCAGATTGTAAACAAATTCTGAAAGCATTAGGACCAGAAG 1834
1101 gaattcaaacccagattgtaaacaaattctgaaagcattaggaccaggag 1150

1835 CTACTTTAGAAGAAATGATGGTAGCCTGTCAAGGAGTAGGAGGGCCAACT 1884
1151 ctactttagaagaaatgatggtagcctgtcaaggagtaggagggccaact 1200

1885 CACAAGGCAAAAATACTAGCAGAAGCAATGGCTTCTGCCCAGCAAGATTT 1934
1201 cacaaggcaaaaatactagcagaagcaatggcttctgcccagcaagattt 1250

1935 AAAAGGAGGATACACAGCAGTATTCATGCAAAGAGGGCAGAATCCAAATA 1984
1251 aaagggaggatacacagcagtattcatgcaaagagggcagaatccaaata 1300

1985 GAAAGGGCCCATAAAATGCTTCAATTGTGGAAAAGAGGGACATATAGCA 2034
1301 gaaagggcctataaaatgtttcaattgtggaaaagagggacatatagca 1350

2035 AAAAACTGTCGAGCACCTAGAAAAAGGGGTTGCTGGAAATGTGGACAGGA 2084
1351 aaaaactgtcgagcacctagaagaaggggttactggaaatgtggacagga 1400

2085 AGGTCACCAAATGAAAGATTGCAAAAATGGAAGACAGGCAAATTTTTTAG 2134
1401 aggtcaccaaatgaaagattgcaaaaatggaagacaggctaattttttag 1450

2135 GGAAGTACTGGCCTCCGGGGGGCACGAGGCCAGGCAATTATGTGCAGAAA 2184
1451 ggaagtactggcctccggggggcacgaggccagccaattatgtgcagaaa 1500

FIG. 6-3

```
2185 CAAGTGTCCCCATCAGCCCCACCAATGGAGGAGGCAGTGAAGGAACAAGA 2234
     ||||||||||||||||||||||||||||||||||||||||||||||||||
1501 caagtgtccccatcagccccaccaatggaggaggcagtgaaggaacaaga 1550

2235 GAATCAGAGTCAGAAGGGGGATCAGGAAGAGCTGTACCCATTTGCCTCCC 2284
     ||||||||| ||| ||||||||||||||||||||||||||||||||||||
1551 gaatcagaatcaaaagggggatcaggaagagctgtacccatttgcctccc 1600

2285 TCAAATCCCTCTTTGGGACAGACCAATAGTCACAGCAAAGGTTGGGGGTC 2334
     ||||||||||||||||||||||||||||||||||||||||||||||||| |
1601 tcaaatccctctttgggacagaccaatagtcacagcaaaggttgggggcc 1650

2335 ATCTATGTGAGGCTTTACTGGATACAGGGGCAGATGATACAGTATTAAAT 2384
     ||||||||||||||||||||||||||||||||||||||||||||||||||
1651 atctatgtgaggctttactggatacaggggcagatgatacagtattaaat 1700

2385 AACATACAATTAGAAGGAAGATGGACACCAAAA 2417
     ||||||||||||||||||||||||||||| |||
1701 aacatacaattagaaggaagatggacacccaaa 1733
```

FIG. 6-4

(SEQ. ID NO. 59 + 60)

```
MvP5180  MGARASVLTGSKLDAWERIRLRPGSKKAYRLKHLVWASRELERYACNPGL
         ||||:|||||||||||||||||||||||||||||||||||||||:||||
    PCR  MGARRSVLTGSKLDAWERIRLRPGSKKAYRLKHLVWASRELERYAYNPGL

LETAEGTEQLLQQLEPALKTGSEDLKSLWNAIAVLWCVHNRFDIRDTQQA
         ||||||||||||||||||||||||||||||||||||||||||||||||||
         LETAEGTEQLLQQLEPALKTGSEDLKSLWNAIAVLWCVHNRFDIRDTQQA

IQKLKEVMASRKSAEAAKEETSPRQTSQNYPIVTNAQGQMVHQAISPRTL
         |||||||||||||||||||||||:||:|||||||||||||||||||||||
         IQKLKEVMASRKSAEAAKEETSSTQASQNYPIVTNAQGQMVHQAISPRTL

NAWVKAVEEKAFNPEIIPMFMALSEGAVPYDINTMLNAIGGHQGALQVLK
         ||||||||||||||||||||||||||||||||||||||||||||||||||
         NAWVKAVEEKAFNPEIIPMFMALSEGAVPYDINTMLNAIGGHQGALQVLK

EVINEEAAEWDRTHPPAMGPLPPGQIREPTGSDIAGTTSTQQEQIIWTTR
         |||||||:||||||||||||||||||||||||||||||||||||||||||
         EVINEEAADWDRTHPPAMGPLPPGQIREPTGSDIAGTTSTQQEQIIWTTR

GANSIPVGDIYRKWIVLGLNKMVKMYSPVSILDIRQGPKEPFRDYVDRFY
         ||||||||||||||||||||||||||||||||||||||||||||||||||
         GANSIPVGDIYRKWIVLGLNKMVKMYSPVSILDIRQGPKEPFRDYVDRFY

KTLRAEQATQEVKNWMTETLLVQNSNPDCKQILKALGPEATLEEMMVACQ
         |||||||||||||||||||||:||||||||||||||||||:|||||||||
         KTLRAEQATQEVKNWMTETLVVQNSNPDCKQILKALGPGATLEEMMVACQ

GVGGPTHKAKILAEAMASAQQDLKGGYTAVFMQRGQNPNRKGPIKCFNCG
         ||||||||||||||||||||||||||||||||||||||||||||||||||
         GVGGPTHKAKILAEAMASAQQDLKGGYTAVFMQRGQNPNRKGPIKCFNCG

KEGHIAKNCRAPRKRGCWKCGQEGHQMKDCKNGRQANFLGKYWPPGGTRP
         |||||||||||||:||:|||||||||||||||||||||||||||||||||
         KEGHIAKNCRAPRRRGYWKCGQEGHQMKDCKNGRQANFLGKYWPPGGTRP

GNYVQKQVSPSAPPMEEAVKEQENQSQKGDQEELYPFASLKSLFGTDQ
         :|||||||||||||||||||||||||:|||||||||||||||||||||
         ANYVQKQVSPSAPPMEEAVKEQENQNQKGDQEELYPFASLKSLFGTDQ
```

FIG. 7

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CTACTAGTAC CCTTCAGG                                                                                   18

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGGTCTACAT AGTCTCTAAA G                                                                               21

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCACCTATCC CAGTAGGAGA A                                                                               21

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCTTTGGTCC TTGTCTTATG TCCAGAATGC                                                                      30

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TGGGAAGTTC AATTAGGAAT ACCAC                                                                           25

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCTACATAGA AATCATCCAT GTATTG                                                                          26

(2) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

TGGATGTGGG TGATGCATA　　　　　　　　　　　　　　　　　　　　　　　　19

( 2 ) INFORMATION FOR SEQ ID NO:8:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

AGCACATTGT ACTGATATCT A　　　　　　　　　　　　　　　　　　　　　　21

( 2 ) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

AGTGGGGGGA CATCAAGCAG CC　　　　　　　　　　　　　　　　　　　　22

( 2 ) INFORMATION FOR SEQ ID NO:10:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

TGCTATGTCA CTTCCCCTTG GT　　　　　　　　　　　　　　　　　　　　22

( 2 ) INFORMATION FOR SEQ ID NO:11:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CCATGCAAAT GTTAAAAGAG AC　　　　　　　　　　　　　　　　　　　　22

( 2 ) INFORMATION FOR SEQ ID NO:12:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear (ii) MOLECULE TYPE: DNA (genomic)

(xi) SEQUENCE DESCRIPTION: SEQ ID NO:12:

GGCCTGGTGC AATAGGCCC 19

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTGCTTCCAC AGGGATGGAA 20

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ATCATCCATG TATTGATA 18

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AATGGAGCCA GTAGATCCTA 20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGTCTCCGCT TCTTCCTGCC 20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GAGCCCTGGA AGCATCCAGG 20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GGAGATGCCT AAGGCTTTTG 20

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TGTTCCTTGG GTTCTTG 17

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GAGTTTTCCA GAGCAACCCC 20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AGCAGCAGGA AGCACTATGG 20

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GCCCCAGACT GTGAGTTGCA ACAG 24

(2) INFORMATION FOR SEQ ID NO:23:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

GCACAGTACA ATGTACACAT GG 22

( 2 ) INFORMATION FOR SEQ ID NO:24:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

CAGTAGAAAA ATTCCCCTCC AC 22

( 2 ) INFORMATION FOR SEQ ID NO:25:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

TCAGGATCCA TGGGCAGTCT AGCAGAAGAA G 31

( 2 ) INFORMATION FOR SEQ ID NO:26:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

ATGCTCGAGA ACTGCAGCAT CGATTCTGGG TCCCCTCCTG AG 42

( 2 ) INFORMATION FOR SEQ ID NO:27:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

CGAGAACTGC AGCATCGATG CTGCTCCCAA GAACCCAAGG 40

( 2 ) INFORMATION FOR SEQ ID NO:28:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

GGAGCTGCTT GATGCCCCAG A    21

( 2 ) INFORMATION FOR SEQ ID NO:29:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TGATGACAGC ATGTCAGGGA GT    22

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GCTGACATTT ATCACAGCTG GCTAC    25

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TATCACCTAG AACTTTAAAT GCATGGG    27

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

AGTCCCTGAC ATGCTGTCAT CA    22

( 2 ) INFORMATION FOR SEQ ID NO:33:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GTGGAGGGGA ATTTTTCTAC TG 22

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CCTGCTGCTC CCAAGAACCC AAGG 24

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

AGCAGCAGGA AGCACTATGG 20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GAGTTTTCCA GAGCAACCCC 20

(2) INFORMATION FOR SEQ ID NO:37:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

GCGCAGCGGC AACAGCGCTG ACGTACGGA CCCACAGTGT ACTGAAGGGT ATAGTGCAAC 60

AGCAGGACAA CCTGCTGAGA GCGATACAGG CCCAGCAACA CTTGCTGAGG TTATCTGTAT 120

GGGGTATTAG ACAACTCCGA GCTCGCCTGC AAGCCTTAGA AACCCTTATA CAGAATCAGC 180

AACGCCTAAA CCTAT 195

(2) INFORMATION FOR SEQ ID NO:38:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
CGCGTCGCCG  TTGTCGCGAC  TGCCATGCCT  GGGTGTCACA  TGACTTCCCA  TATCACGTTG      60

TCGTCCTGTT  GGACGACTCT  CGCTATGTCC  GGGTCGTTGT  GAACGACTCC  AATAGACATA     120

CCCCATAATC  TGTTGAGGCT  CGAGCGGACG  TTCGGAATCT  TTGGGAATAT  GTCTTAGTCG     180

TTGCGGATTT  GGATA                                                         195
```

(2) INFORMATION FOR SEQ ID NO:39:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:39:

```
Ala  Ala  Ala  Thr  Ala  Leu  Thr  Val  Arg  Thr  His  Ser  Val  Leu  Lys  Gly
 1              5                        10                       15

Ile  Val  Gln  Gln  Gln  Asp  Asn  Leu  Leu  Arg  Ala  Ile  Gln  Ala  Gln  Gln
              20                        25                       30

His  Leu  Leu  Arg  Leu  Ser  Val  Trp  Gly  Ile  Arg  Gln  Leu  Arg  Ala  Arg
         35                        40                       45

Leu  Gln  Ala  Leu  Glu  Thr  Leu  Ile  Gln  Asn  Gln  Gln  Arg  Leu  Asn  Leu
    50                        55                       60
```

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
CAGAATCAGC  AACGCCTAAA  CC                                                  22
```

(2) INFORMATION FOR SEQ ID NO:41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
GCCCTGTCTT  ATTCTTCTAG  G                                                   21
```

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
GCCTGCAAGC  CTTAGAAACC                                                      20
```

(2) INFORMATION FOR SEQ ID NO:43:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
GCACTATACC CTTCAGTACA CTG                                              23
```

(2) INFORMATION FOR SEQ ID NO:44:

(i) SEQUENCE CHARACTERISTICS:
        (A) LENGTH: 1057 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
AAATGTCAAG ACCAATAATA AACATTCACA CCCCTCACAG GGAAAAAAGA CGAGTAGGAT      60
TGGGAATGCT ATTCTTGGGG GTGCTAAGTG CAGCAGGTAG CACTATGGGC GCAGCGGCAA     120
CAGCGCTGAC GGTACGGACC CACAGTGTAC TGAAGGGTAT AGTGCAACAG CAGGACAACC     180
TGCTGAGAGC GATACAGGCC CAGCAACACT TGCTGAGGTT ATCTGTATGG GGTATTAGAC     240
AACTCCGAGC TCGCCTGCAA GCCTTAGAAA CCCTTATACA GAATCAGCAA CGCCTAAACC     300
TATGGGGCTG TAAAGGAAAA CTAATCTGTT ACACATCAGT AAAATGGAAC ACATCATGGT     360
CAGGAGGATA TAATGATGAC AGTATTTGGG ACAACCTTAC ATGGCAGCAA TGGGACCAAC     420
ACATAAACAA TGTAAGCTCC ATTATATATG ATGAAATACA AGCAGCACAA GACCAACAGG     480
AAAAGAATGT AAAAGCATTG TTGGAGCTAG ATGAATGGGC CTCTCTTTGG AATTGGTTTG     540
ACATAACTAA ATGGTTGTGG TATATAAAAA TAGCTATAAT CATAGTGGGA GCACTAATAG     600
GTATAAGAGT TATCATGATA GTACTTAATC TAGTGAAGAA CATTAGGCAG GGATATCAAC     660
CCCTCTCGTT GCAGATCCCT GTCCCACACC GGCAGGAAGC AGAAACGCCA GGAAGAACAG     720
GAGAAGAAGG TGGAGAAGGA GACAGGCCCA AGTGGACAGC CTTGCCACCA GGATTCTTGC     780
AACAGTTGTA CACGGATCTC AGGACAATAA TCTTGTGGAC TTACCACCTC TTGAGCAACT     840
TAATATCAGG GATCCGGAGG CTGATCGACT ACCTGGGACT GGGACTGTGG ATCCTGGGAC     900
AAAAGACAAT TGAAGCTTGT AGACTTTGTG GAGCTGTAAT GCAATATTGG CTACAAGAAT     960
TGAAAAATAG TGCTACAAAC CTGCTTGATA CTATTGCAGT GTCAGTTGCC AATTGGACTG    1020
ACGGCATCAT CTTAGGTCTA CAAAGAATAG GACAAGG                             1057
```

(2) INFORMATION FOR SEQ ID NO:45:

(i) SEQUENCE CHARACTERISTICS:
        (A) LENGTH: 1057 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
TTTACAGTTC TGGTTATTAT TTGTAAGTGT GGGGAGTGTC CCTTTTTTCT CGTCATCCTA      60
ACCCTTACGA TAAGAACCCC CACGATTCAC GTCGTCCATC GTGATACCCG CGTCGCCGTT     120
```

```
GTCGCGACTG CCATGCCTGG GTGTCACATG ACTTCCCATA TCACGTTGTC GTCCTGTTGG      180

ACGACTCTCG CTATGTCCGG GTCGTTGTGA ACGACTCCAA TAGACATACC CCATAATCTG      240

TTGAGGCTCG AGCGGACGTT CGGAATCTTT GGGAATATGT CTTAGTCGTT GCGGATTTGG      300

ATACCCCGAC ATTTCCTTTT GATTAGACAA TGTGTAGTCA TTTTACCTTG TGTAGTACCA      360

GTCCTCCTAT ATTACTACTG TCATAAACCC TGTTGGAATG TACCGTCGTT ACCCTGGTTG      420

TGTATTTGTT ACATTCGAGG TAATATATAC TACTTTATGT TCGTCGTGTT CTGGTTGTCC      480

TTTTCTTACA TTTTCGTAAC AACCTCGATC TACTTACCCG GAGAGAAACC TTAACCAAAC      540

TGTATTGATT TACCAACACC ATATATTTTT ATCGATATTA GTATCACCCT CGTGATTATC      600

CATATTCTCA ATAGTACTAT CATGAATTAG ATCACTTCTT GTAATCCGTC CCTATAGTTG      660

GGGAGAGCAA CGTCTAGGGA CAGGGTGTGG CCGTCCTTCG TCTTTGCGGT CCTTCTTGTC      720

CTCTTCTTCC ACCTCTTCCT CTGTCCGGGT TCACCTGTCG GAACGGTGGT CCTAAGAACG      780

TTGTCAACAT GTGCCTAGAG TCCTGTTATT AGAACACCTG AATGGTGGAG AACTCGTTGA      840

ATTATAGTCC CTAGGCCTCC GACTAGCTGA TGGACCCTGA CCCTGACACC TAGGACCCTG      900

TTTTCTGTTA ACTTCGAACA TCTGAAACAC CTCGACATTA CGTTATAACC GATGTTCTTA      960

ACTTTTTATC ACGATGTTTG GACGAACTAT GATAACGTCA CAGTCAACGG TTAACCTGAC     1020

TGCCGTAGTA GAATCCAGAT GTTTCTTATC CTGTTCC                              1057
```

(2) INFORMATION FOR SEQ ID NO:46:

(i) SEQUENCE CHARACTERISTICS:
        (A) LENGTH: 351 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:46:

```
Met Ser Arg Pro Ile Ile Asn Ile His Thr Pro His Arg Glu Lys Arg
 1               5                  10                  15

Ala Val Gly Leu Gly Met Leu Phe Leu Gly Val Leu Ser Ala Ala Gly
             20                  25                  30

Ser Thr Met Gly Ala Ala Ala Thr Ala Leu Thr Val Arg Thr His Ser
         35                  40                  45

Val Leu Lys Gly Ile Val Gln Gln Asp Asn Leu Leu Arg Ala Ile
     50                  55                  60

Gln Ala Gln Gln His Leu Leu Arg Leu Ser Val Trp Gly Ile Arg Gln
 65                  70                  75                  80

Leu Arg Ala Arg Leu Gln Ala Leu Glu Thr Leu Ile Gln Asn Gln Gln
                 85                  90                  95

Arg Leu Asn Leu Trp Gly Cys Lys Gly Lys Leu Ile Cys Tyr Thr Ser
            100                 105                 110

Val Lys Trp Asn Thr Ser Trp Ser Gly Gly Tyr Asn Asp Asp Ser Ile
            115                 120                 125

Trp Asp Asn Leu Thr Trp Gln Gln Trp Asp Gln His Ile Asn Asn Val
        130                 135                 140

Ser Ser Ile Ile Tyr Asp Glu Ile Gln Ala Ala Gln Asp Gln Gln Glu
145                 150                 155                 160

Lys Asn Val Lys Ala Leu Leu Glu Leu Asp Glu Trp Ala Ser Leu Trp
                165                 170                 175
```

| | | | | | | | | | | | | | | |
|---|---|---|---|---|---|---|---|---|---|---|---|---|---|---|
| Asn | Trp | Phe | Asp<br>180 | Ile | Thr | Lys | Trp<br>185 | Leu | Trp | Tyr | Ile | Lys<br>190 | Ile | Ala | Ile |
| Ile | Ile | Val<br>195 | Gly | Ala | Leu | Ile<br>200 | Gly | Ile | Arg | Val | Ile<br>205 | Met | Ile | Val | Leu |
| Asn | Leu | Val<br>210 | Lys | Asn | Ile | Arg<br>215 | Gln | Gly | Tyr | Gln | Pro<br>220 | Leu | Ser | Leu | Gln |
| Ile<br>225 | Pro | Val | Pro | His | Arg<br>230 | Gln | Glu | Ala | Glu | Thr<br>235 | Pro | Gly | Arg | Thr | Gly<br>240 |
| Glu | Glu | Gly | Gly | Glu<br>245 | Gly | Asp | Arg | Pro | Lys<br>250 | Trp | Thr | Ala | Leu | Pro<br>255 | Pro |
| Gly | Phe | Leu | Gln<br>260 | Gln | Leu | Tyr | Thr | Asp<br>265 | Leu | Arg | Thr | Ile | Ile<br>270 | Leu | Trp |
| Thr | Tyr | His<br>275 | Leu | Leu | Ser | Asn | Leu<br>280 | Ile | Ser | Gly | Ile | Arg<br>285 | Arg | Leu | Ile |
| Asp | Tyr | Leu<br>290 | Gly | Leu | Gly | Leu<br>295 | Trp | Ile | Leu | Gly | Gln<br>300 | Lys | Thr | Ile | Glu |
| Ala<br>305 | Cys | Arg | Leu | Cys | Gly<br>310 | Ala | Val | Met | Gln | Tyr<br>315 | Trp | Leu | Gln | Glu | Leu<br>320 |
| Lys | Asn | Ser | Ala | Thr<br>325 | Asn | Leu | Leu | Asp | Thr<br>330 | Ile | Ala | Val | Ser | Val<br>335 | Ala |
| Asn | Trp | Thr | Asp<br>340 | Gly | Ile | Ile | Leu | Gly<br>345 | Leu | Gln | Arg | Ile | Gly<br>350 | Gln | |

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CTAGCAGTGG CGCCCGAACA GG        22

( 2 ) INFORMATION FOR SEQ ID NO:48:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

AATGAGGAAG CUGCAGAUTG GGA        23

( 2 ) INFORMATION FOR SEQ ID NO:49:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

TCCCAUTCTG CUGCTTCCTC ATT        23

( 2 ) INFORMATION FOR SEQ ID NO:50:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:50:

CCAAGGGGAA GTGACATAGC AGGAAC    26

( 2 ) INFORMATION FOR SEQ ID NO:51:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:51:

CGTTGTTCAG AATTCAAACC C    21

( 2 ) INFORMATION FOR SEQ ID NO:52:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:52:

TCCCTAAAAA ATTAGCCTGT C    21

( 2 ) INFORMATION FOR SEQ ID NO:53:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:53:

AAACCTCCAA TTCCCCTA    19

( 2 ) INFORMATION FOR SEQ ID NO:54:

( i ) SEQUENCE CHARACTERISTICS:
    ( A ) LENGTH: 39 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:54:

Cys Ile Arg Glu Gly Ile Ala Glu Val Gln Asp Ile Tyr Thr Gly Pro
1     5       10       15

Met Arg Trp Arg Ser Met Thr Leu Lys Arg Ser Asn Asn Thr Ser Pro
    20      25      30

Arg Ser Arg Val Ala Tyr Cys
   35

(2) INFORMATION FOR SEQ ID NO:55:

(i) SEQUENCE CHARACTERISTICS:
        (A) LENGTH: 41 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:55:

```
Cys Ile Arg Glu Gly Ile Ala Glu Val Gln Asp Leu His Thr Gly Pro
 1               5                  10                     15

Leu Arg Trp Arg Ser Met Thr Leu Lys Lys Ser Ser Asn Ser His Thr
                20              25                  30

Gln Pro Arg Ser Lys Val Ala Tyr Cys
                35              40
```

(2) INFORMATION FOR SEQ ID NO:56:

(i) SEQUENCE CHARACTERISTICS:
        (A) LENGTH: 9793 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

```
CTGGATGGGT TAATTTACTC CCATAAGAGA GCAGAAATCC TGGATCTCTG GATATATCAC      60
ACTCAGGGAT TCTTCCCTGA TTGGCAGTGT TACACACCGG GACCAGGACC TAGATTCCCA     120
CTGACATTTG GATGGTTGTT TAAACTGGTA CCAGTGTCAG CAGAAGAGGC AGAGAGACTG     180
GGTAATACAA ATGAAGATGC TAGTCTTCTA CATCCAGCTT GTAATCATGG AGCTGAGGAT     240
GCACACGGGG AGATACTAAA ATGGCAGTTT GATAGATCAT TAGGCTTAAC ACATATAGCC     300
CTGCAAAAGC ACCCAGAGCT CTTCCCCAAG TAACTGACAC TGCGGGACTT TCCAGACTGC     360
TGACACTGCG GGACTTTCC AGCGTGGGAG GGATAAGGGG CGGTTCGGGG AGTGGCTAAC     420
CCTCAGATGC TGCATATAAG CAGCTGCTTT CCGCTTGTAC CGGGTCTTAG TTAGAGGACC     480
AGGTCTGAGC CCGGGAGCTC CCTGGCCTCT AGCTGAACCC GCTGCTTAAC GCTCAATAAA     540
GCTTGCCTTG AGTGAGAAGC AGTGTGTGCT CATCTGTTCA ACCCTGGTGT CTAGAGATCC     600
CTCAGATCAC TTAGACTGAA GCAGAAAATC TCTAGCAGTG GCGCCCGAAC AGGGACGCGA     660
AAGTGAAAGT GGAACCAGGG AAGAAAACCT CCGACGCAAC GGGCTCGGCT TAGCGGAGTG     720
CACCTGCTAA GAGGCGAGAG GAACTCACAA GAGGGTGAGT AAATTTGCTG GCGGTGGCCA     780
GACCTAGGGG AAGGGCGAAG TCCCTAGGGG AGGAAGATGG GTGCGAGAGC GTCTGTGTTG     840
ACAGGGAGTA AATTGGATGC ATGGGAACGA ATTAGGTTAA GGCCAGGATC TAAAAAGGCA     900
TATAGGCTAA AACATTTAGT ATGGGCAAGC AGGGAGCTGG AAAGATACGC ATGTAATCCT     960
GGTCTATTAG AAACTGCAGA AGGTACTGAG CAACTGCTAC AGCAGTTAGA GCCAGCTCTC    1020
AAGACAGGGT CAGAGGACCT GAAATCTCTC TGGAACGCAA TAGCAGTACT CTGGTGCGTT    1080
CACAACAGAT TTGACATCCG AGATACACAG CAGGCAATAC AAAAGTTAAA GGAAGTAATG    1140
GCAAGCAGGA AGTCTGCAGA GGCCGCTAAG GAAGAAACAA GCCCTAGGCA GACAAGTCAA    1200
AATTACCCTA TAGTAACAAA TGCACAGGGA CAAATGGTAC ATCAAGCCAT CTCCCCAGG    1260
ACTTTAAATG CATGGGTAAA GGCAGTAGAA GAGAAGGCCT TTAACCCTGA AATTATTCCT    1320
```

| | | | | | |
|---|---|---|---|---|---|
| ATGTTTATGG | CATTATCAGA | AGGGGCTGTC | CCCTATGATA | TCAATACCAT | GCTGAATGCC | 1380
| ATAGGGGGAC | ACCAAGGGGC | TTTACAAGTG | TTGAAGGAAG | TAATCAATGA | GGAAGCAGCA | 1440
| GAATGGGATA | GAACTCATCC | ACCAGCAATG | GGGCCGTTAC | CACCAGGGCA | GATAAGGGAA | 1500
| CCAACAGGAA | GTGACATTGC | TGGAACAACT | AGCACACAGC | AAGAGCAAAT | TATATGGACT | 1560
| ACTAGAGGGG | CTAACTCTAT | CCCAGTAGGA | GACATCTATA | GAAAATGGAT | AGTGCTAGGA | 1620
| CTAAACAAAA | TGGTAAAAAT | GTACAGTCCA | GTGAGCATCT | TAGATATTAG | GCAGGGACCA | 1680
| AAAGAACCAT | TCAGAGATTA | TGTAGATCGG | TTTTACAAAA | CATTAAGAGC | TGAGCAAGCT | 1740
| ACTCAAGAAG | TAAAGAATTG | GATGACAGAA | ACCTTGCTTG | TTCAGAATTC | AAACCCAGAT | 1800
| TGTAAACAAA | TTCTGAAAGC | ATTAGGACCA | GAAGCTACTT | TAGAAGAAAT | GATGGTAGCC | 1860
| TGTCAAGGAG | TAGGAGGGCC | AACTCACAAG | GCAAAATAC | TAGCAGAAGC | AATGGCTTCT | 1920
| GCCCAGCAAG | ATTTAAAAGG | AGGATACACA | GCAGTATTCA | TGCAAAGAGG | GCAGAATCCA | 1980
| AATAGAAAAG | GGCCCATAAA | ATGCTTCAAT | TGTGGAAAAG | AGGGACATAT | AGCAAAAAAC | 2040
| TGTCGAGCAC | CTAGAAAAAG | GGGTTGCTGG | AAATGTGGAC | AGGAAGGTCA | CCAAATGAAA | 2100
| GATTGCAAAA | ATGGAAGACA | GGCAAATTTT | TTAGGGAAGT | ACTGGCCTCC | GGGGGGCACG | 2160
| AGGCCAGGCA | ATTATGTGCA | GAAACAAGTG | TCCCCATCAG | CCCCACCAAT | GGAGGAGGCA | 2220
| GTGAAGGAAC | AAGAGAATCA | GAGTCAGAAG | GGGGATCAGG | AAGAGCTGTA | CCCATTTGCC | 2280
| TCCCTCAAAT | CCCTCTTTGG | GACAGACCAA | TAGTCACAGC | AAAGGTTGGG | GGTCATCTAT | 2340
| GTGAGGCTTT | ACTGGATACA | GGGGCAGATG | ATACAGTATT | AAATAACATA | CAATTAGAAG | 2400
| GAAGATGGAC | ACCAAAAATG | ATAGGGGGTA | TAGGAGGCTT | TATAAAAGTA | AAAGAGTATA | 2460
| ACAATGTGAC | AGTAGAAGTA | CAAGGAAAGG | AAGTACAGGG | AACAGTATTG | GTGGGACCTA | 2520
| CTCCTGTTAA | TATTCTTGGG | AGAAACATAT | TGACAGGATT | AGGATGTACA | CTAAATTTCC | 2580
| CTATAAGTCC | CATAGCCCCA | GTGCCAGTAA | AGCTAAAACC | AGGAATGGAT | GGACCAAAAG | 2640
| TAAAACAATG | GCCCCTATCT | AGAGAGAAAA | TAGAAGCACT | AACTGCAATA | TGTCAAGAAA | 2700
| TGGAACAGGA | AGGAAAAATC | TCAAGAATAG | GACCTGAAAA | TCCTTATAAT | ACACCTATTT | 2760
| TTGCTATAAA | AAAGAAAGAT | AGCACTAAGT | GGAGAAAATT | GGTAGACTTC | AGAGAATTAA | 2820
| ATAAAAGAAC | ACAAGATTTC | TGGGAGGTGC | AATTAGGTAT | TCCACATCCA | GGGGGTTTAA | 2880
| AGCAAAGGCA | ATCTGTTACA | GTCTTAGATG | TAGGAGATGC | TTATTTCTCA | TGCCCTTTAG | 2940
| ATCCAGACTT | TAGAAAATAC | ACTGCCTTCA | CTATTCCTAG | TGTGAACAAT | GAGACCCCAG | 3000
| GAGTAAGATA | CCAGTACAAT | GTCCTCCCGC | AAGGGTGGAA | AGGTTCACCA | GCCATATTTC | 3060
| AGAGTTCAAT | GACAAAGATT | CTAGATCCAT | TTAGAAAAAG | CAACCCAGAA | GTAGAAATTT | 3120
| ATCAGTACAT | AGATGACTTA | TATGTAGGAT | CAGATTTACC | ATTGGCAGAA | CATAGAAAGA | 3180
| GGGTCGAATT | GCTTAGGGAA | CATTTATATC | AGTGGGGATT | TACTACCCCT | GATAAAAAGC | 3240
| ATCAGAAGGA | ACCTCCCTTT | TTATGGATGG | GATATGAGCT | CCACCCAGAC | AAGTGGACAG | 3300
| TACAGCCCAT | CCAATTGCCT | GACAAAGAAG | TGTGGACAGT | AAATGATATA | CAAAAATTAG | 3360
| TAGGAAAATT | AAATTGGGCA | AGTCAAATCT | ATCAAGGAAT | TAGAGTAAAA | GAATTGTGCA | 3420
| AGTTAATCAG | AGGAACCAAA | TCATTGACAG | AGGTAGTACC | TTTAAGTAAA | GAGGCAGAAC | 3480
| TAGAATTAGA | AGAAAACAGA | GAAAAGCTAA | AAGAGCCAGT | ACATGGAGTA | TATTACCAGC | 3540
| CTGACAAAGA | CTTGTGGGTT | AGTATTCAGA | AGCATGGAGA | AGGGCAATGG | ACTTACCAGG | 3600
| TATATCAGGA | TGAACATAAG | AACCTTAAAA | CAGGAAAATA | TGCTAGGCAA | AAGGCCTCCC | 3660
| ACACAAATGA | TATAAGACAA | TTGGCAGAAG | TAGTCCAGAA | GGTGTCTCAA | GAAGCTATAG | 3720

| | | | | | | |
|---|---|---|---|---|---|---|
|TTATATGGGG|GAAATTACCT|AAATTCAGGC|TGCCAGTTAC|TAGAGAAACT|TGGGAAACTT|3780|
|GGTGGGCAGA|ATATTGGCAG|GCCACCTGGA|TTCCTGAATG|GGAATTTGTC|AGCACACCCC|3840|
|CATTGATCAA|ATTATGGTAC|CAGTTAGAAA|CAGAACCTAT|TGTAGGGGCA|GAAACCTTTT|3900|
|ATGTAGATGG|AGCAGCTAAT|AGGAATACAA|AACTAGGAAA|GGCGGGATAT|GTTACAGAAC|3960|
|AAGGAAAACA|GAACATAATA|AAGTTAGAAG|AGACAACCAA|TCAAAAGGCT|GAATTAATGG|4020|
|CTGTATTAAT|AGCCTTGCAG|GATTCCAAGG|AGCAAGTAAA|CATAGTAACA|GACTCACAAT|4080|
|ATGTATTGGG|CATCATATCC|TCCCAACCAA|CACAGAGTGA|CTCCCCTATA|GTTCAGCAGA|4140|
|TAATAGAGGA|ACTAACAAAA|AAGGAACGAG|TGTATCTTAC|ATGGGTTCCT|GCTCACAAAG|4200|
|GCATAGGAGG|AAATGAAAAA|ATAGATAAAT|TAGTAAGCAA|AGACATTAGA|AGAGTCCTGT|4260|
|TCCTGGAAGG|AATAGATCAG|GCACAAGAAG|ATCATGAAAA|ATATCATAGT|AATTGGAGAG|4320|
|CATTAGCTAG|TGACTTTGGA|TTACCACCAA|TAGTAGCCAA|GGAAATCATT|GCTAGTTGTC|4380|
|CTAAATGCCA|TATAAAGGG|GAAGCAACGC|ATGGTCAAGT|AGACTACAGC|CCAGAGATAT|4440|
|GGCAAATGGA|TTGTACACAT|TTAGAAGGCA|AAATCATAAT|AGTTGCTGTC|CATGTAGCAA|4500|
|GTGACTTTAT|AGAAGCAGAG|GTGATACCAG|CAGAAACAGG|ACAGGAAACT|GCCTATTTCC|4560|
|TGTTAAAATT|AGCAGCAAGA|TGGCCTGTCA|AAGTAATACA|TACAGACAAT|GGACCTAATT|4620|
|TTACAAGTGC|AGCCATGAAA|GCTGCATGTT|GGTGGACAGG|CATACAACAT|GAGTTTGGGA|4680|
|TACCATATAA|TCCACAAAGT|CAAGGAGTAG|TAGAAGCCAT|GAATAAAGAA|TTAAAATCTA|4740|
|TTATACAGCA|GGTGAGGGAC|CAAGCAGAGC|ATTTAAAAAC|AGCAGTACAA|ATGGCAGTCT|4800|
|TTGTTCACAA|TTTTAAAAGA|AAAGGGGGGA|TTGGGGGGTA|CACTGCAGGG|GAGAGACTAA|4860|
|TAGACATACT|AGCATCACAA|ATACAAACAA|CAGAACTACA|AAAACAAATT|TAAAAATCA|4920|
|ACAATTTTCG|GGTCTATTAC|AGAGATAGCA|GAGACCCTAT|TTGGAAAGGA|CCGGCACAAC|4980|
|TCCTGTGGAA|AGGTGAGGGG|GCAGTAGTCA|TACAAGATAA|AGGAGACATT|AAAGTGGTAC|5040|
|CAAGAAGAAA|GGCAAAAATA|ATCAGAGATT|ATGGAAAACA|GATGGCAGGT|ACTGATAGTA|5100|
|TGGCAAATAG|ACAGACAGAA|AGTGAAAGCA|TGGAACAGCC|TGGTGAAATA|CCATAAATAC|5160|
|ATGTCTAAGA|AGGCCGCGAA|CTGGCGTTAT|AGGCATCATT|ATGAATCCAG|GAATCCAAAA|5220|
|GTCAGTTCGG|CGGTGTATAT|TCCAGTAGCA|GAAGCTGATA|TAGTGGTCAC|CACATATTGG|5280|
|GGATTAATGC|CAGGGGAAAG|AGAGGAACAC|TTGGGACATG|GGGTTAGTAT|AGAATGGCAA|5340|
|TACAAGGAGT|ATAAAACACA|GATTGATCCT|GAAACAGCAG|ACAGGATGAT|ACATCTGCAT|5400|
|TATTTCACAT|GTTTTACAGA|ATCAGCAATC|AGGAAGGCCA|TTCTAGGGCA|GAGAGTGCTG|5460|
|ACCAAGTGTG|AATACCTGGC|AGGACATAGT|CAGGTAGGGA|CACTACAATT|CTTAGCCTTG|5520|
|AAAGCAGTAG|TGAAAGTAAA|AAGAAATAAG|CCTCCCCTAC|CCAGTGTCCA|GAGATTAACA|5580|
|GAAGATAGAT|GGAACAAGCC|CTGGAAAATC|AGGGACCAGC|TAGGGAGCCA|TTCAATGAAT|5640|
|GGACACTAGA|GCTCCTGGAA|GAGCTGAAAG|AAGAAGCAGT|AAGACATTTC|CCTAGGCCTT|5700|
|GGTTACAAGC|CTGTGGGCAG|TACATTTATG|AGACTTATGG|AGACACTTGG|GAAGGAGTTA|5760|
|TGGCAATTAT|AAGAATCTTA|CAACAACTAC|TGTTTACCCA|TTATAGAATT|GGATGCCAAC|5820|
|ATAGTAGAAT|AGGAATTCTC|CCATCTAACA|CAAGAGGAAG|AGGAAGAAGA|AATGGATCCA|5880|
|GTAGATCCTG|AGATGCCCCC|TTGGCATCAC|CCTGGGAGCA|AGCCCCAAAC|CCCTTGTAAT|5940|
|AATTGCTATT|GCAAAAGATG|CTGCTATCAT|TGCTATGTTT|GTTTCACAAA|GAAGGGTTTG|6000|
|GGAATCTCCC|ATGGCAGGAA|GAAGCGAAGA|AGACCAGCAG|CTGCTGCAAG|CTATCCAGAT|6060|
|AATAAAGATC|CTGTACCAGA|GCAGTAAGTA|ACGCTGATGC|ATCAAGAGAA|CCTGCTAGCC|6120|

```
TTAATAGCTT  TAAGTGCTTT  GTGTCTTATA  AATGTACTTA  TATGGTTGTT  TAACCTTAGA      6180

ATTTATTTAG  TGCAAAGAAA  ACAAGATAGA  AGGGAGCAGG  AAATACTTGA  AAGATTAAGG      6240

AGAATAAAGG  AAATCAGGGA  TGACAGTGAC  TATGAAAGTA  ATGAAGAAGA  ACAACAGGAA      6300

GTCATGGAGC  TTATACATAG  CCATGGCTTT  GCTAATCCCA  TGTTTGAGTT  ATAGTAAACA      6360

ATTGTATGCC  ACAGTTTATT  CTGGGGTACC  TGTATGGGAA  GAGGCAGCAC  CAGTACTATT      6420

CTGTGCTTCA  GATGCTAACC  TAACAAGCAC  TGAACAGCAT  AATATTTGGG  CATCACAAGC      6480

CTGCGTTCCT  ACAGATCCCA  ATCCACATGA  ATTTCCACTA  GGCAATGTGA  CAGATAACTT      6540

TGATATATGG  AAAAATTACA  TGGTGGACCA  AATGCATGAA  GACATCATTA  GTTTGTGGGA      6600

ACAGAGTTTA  AAGCCTTGTG  AGAAAATGAC  TTTCTTATGT  GTACAAATGA  ACTGTGTAGA      6660

TCTGCAAACA  AATAAAACAG  GCCTATTAAA  TGAGACAATA  AATGAGATGA  GAAATTGTAG      6720

TTTTAATGTA  ACTACAGTCC  TCACAGACAA  AAAGGAGCAA  AAACAGGCTC  TATTCTATGT      6780

ATCAGATCTG  AGTAAGGTTA  ATGACTCAAA  TGCAGTAAAT  GGAACAACAT  ATATGTTAAC      6840

TAATTGTAAC  TCCACAATTA  TCAAGCAGGC  CTGTCCGAAG  GTAAGTTTTG  AGCCCATTCC      6900

CATACACTAT  TGTGCTCCAA  CAGGATATGC  CATCTTTAAG  TGTAATGACA  CAGACTTTAA      6960

TGGAACAGGC  CTATGCCACA  ATATTTCAGT  GGTTACTTGT  ACACATGGCA  TCAAGCCAAC      7020

AGTAAGTACT  CAACTAATAC  TGAATGGGAC  ACTCTCTAGA  GAAAAGATAA  GAATTATGGG      7080

AAAAATATT  ACAGAATCAG  CAAAGAATAT  CATAGTAACC  CTAAACACTC  CTATAAACAT      7140

GACCTGCATA  AGAGAAGGAA  TTGCAGAGGT  ACAAGATATA  TATACAGGTC  CAATGAGATG      7200

GCGCAGTATG  ACACTTAAAA  GAAGTAACAA  TACATCACCA  AGATCAAGGG  TAGCTTATTG      7260

TACATATAAT  AAGACTGTAT  GGGAAAATGC  CCTACAACAA  ACAGCTATAA  GGTATTTAAA      7320

TCTTGTAAAC  CAAACAGAGA  ATGTTACCAT  AATATTCAGC  AGAACTAGTG  GTGGAGATGC      7380

AGAAGTAAGC  CATTTACATT  TTAACTGTCA  TGGAGAATTC  TTTTATTGTA  ACACATCTGG      7440

GATGTTTAAC  TATACTTTTA  TCAACTGTAC  AAAGTCCGGA  TGCCAGGAGA  TCAAAGGGAG      7500

CAATGAGACC  AATAAAAATG  GTACTATACC  TTGCAAGTTA  AGACAGCTAG  TAAGATCATG      7560

GATGAAGGGA  GAGTCGAGAA  TCTATGCACC  TCCCATCCCC  GGCAACTTAA  CATGTCATTC      7620

CAACATAACT  GGAATGATTC  TACAGTTAGA  TCAACCATGG  AATTCCACAG  GTGAAAATAC      7680

ACTTAGACCA  GTAGGGGGAG  ATATGAAAGA  TATATGGAGA  ACTAAATTGT  ACAACTACAA      7740

AGTAGTACAG  ATAAAACCTT  TTAGTGTAGC  ACCTACAAAA  ATGTCAAGAC  CAATAATAAA      7800

CATTCACACC  CCTCACAGGG  AAAAAGAGC  AGTAGGATTG  GGAATGCTAT  TCTTGGGGT       7860

GCTAAGTGCA  GCAGGTAGCA  CTATGGGCGC  AGCGGCAACA  GCGCTGACGG  TACGGACCCA      7920

CAGTGTACTG  AAGGGTATAG  TGCAACAGCA  GGACAACCTG  CTGAGAGCGA  TACAGGCCCA      7980

GCAACACTTG  CTGAGGTTAT  CTGTATGGGG  TATTAGACAA  CTCCGAGCTC  GCCTGCAAGC      8040

CTTAGAAACC  CTTATACAGA  ATCAGCAACG  CCTAAACCTA  TGGGGCTGTA  AAGGAAAACT      8100

AATCTGTTAC  ACATCAGTAA  AATGGAACAC  ATCATGGTCA  GGAAGATATA  ATGATGACAG      8160

TATTTGGGAC  AACCTTACAT  GGCAGCAATG  GGACCAACAC  ATAAACAATG  TAAGCTCCAT      8220

TATATATGAT  GAAATACAAG  CAGCACAAGA  CCAACAGGAA  AAGAATGTAA  AAGCATTGTT      8280

GGAGCTAGAT  GAATGGGCCT  CTCTTTGGAA  TTGGTTTGAC  ATAACTAAAT  GGTTGTGGTA      8340

TATAAAAATA  GCTATAATCA  TAGTGGGAGC  ACTAATAGGT  ATAAGAGTTA  TTATGATAAT      8400

ACTTAATCTA  GTGAAGAACA  TTAGGCAGGG  ATATCAACCC  CTCTCGTTGC  AGATCCCTGT      8460

CCCACACCGG  CAGGAAGCAG  AAACGCCAGG  AAGAACAGGA  GAAGAAGGTG  GAGAAGGAGA      8520
```

| | | | | | |
|---|---|---|---|---|---|
| CAGGCCCAAG | TGGACAGCCT | TGCCACCAGG | ATTCTTGCAA | CAGTTGTACA | CGGATCTCAG | 8580
| GACAATAATC | TTGTGGACTT | ACCACCTCTT | GAGCAACTTA | ATATCAGGGA | TCCGGAGGCT | 8640
| GATCGACTAC | CTGGGACTGG | GACTGTGGAT | CCTGGGACAA | AAGACAATTG | AAGCTTGTAG | 8700
| ACTTTGTGGA | GCTGTAATGC | AATATTGGCT | ACAAGAATTG | AAAAATAGTG | CTACAAACCT | 8760
| GCTTGATACT | ATTGCAGTGT | CAGTTGCCAA | TTGGACTGAC | GGCATCATCT | TAGGTCTACA | 8820
| AAGAATAGGA | CAAGGATTCC | TTCACATCCC | AAGAAGAATT | AGACAAGGTG | CAGAAAGAAT | 8880
| CTTAGTGTAA | CATGGGGAAT | GCATGGAGCA | AAAGCAAATT | TGCAGGATGG | TCAGAAGTAA | 8940
| GAGATAGAAT | GAGACGATCC | TCCTCTGATC | CTCAACAACC | ATGTGCACCT | GGAGTAGGAG | 9000
| CTGTCTCCAG | GGAGTTAGCA | ACTAGAGGGG | GAATATCAAG | TTCCCACACT | CCTCAAAACA | 9060
| ATGCAGCCCT | TGCATTCCTA | GACAGCCACA | AAGATGAGGA | TGTAGGCTTC | CCAGTAAGAC | 9120
| CTCAAGTGCC | TCTAAGGCCA | ATGACCTTTA | AAGCAGCCTT | TGACCTCAGC | TTCTTTTTAA | 9180
| AAGAAAAGGG | AGGACTGGAT | GGGTTAATTT | ACTCCCATAA | GAGAGCAGAA | ATCCTGGATC | 9240
| TCTGGATATA | TCACACTCAG | GGATTCTTCC | CTGATTGGCA | GTGTTACACA | CCGGGACCAG | 9300
| GACCTAGATT | CCCACTGACA | TTTGGATGGT | TGTTTAAACT | GGTACCAGTG | TCAGCAGAAG | 9360
| AGGCAGAGAG | ACTGGGTAAT | ACAAATGAAG | ATGCTAGTCT | TCTACATCCA | GCTTGTAATC | 9420
| ATGGAGCTGA | GGATGCACAC | GGGGAGATAC | TAAAATGGCA | GTTTGATAGA | TCATTAGGCT | 9480
| TAACACATAT | AGCCCTGCAA | AAGCACCCAG | AGCTCTTCCC | CAAGTAACTG | ACACTGCGGG | 9540
| ACTTTCCAGA | CTGCTGACAC | TGCGGGGACT | TTCCAGCGTG | GAGGGATAA | GGGGCGGTTC | 9600
| GGGGAGTGGC | TAACCCTCAG | ATGCTGCATA | TAAGCAGCTG | CTTTCCGCTT | GTACCGGGTC | 9660
| TTAGTTAGAG | GACCAGGTCT | GAGCCCGGGA | GCTCCTGGC | CTCTAGCTGA | ACCCGCTGCT | 9720
| TAACGCTCAA | TAAAGCTTGC | CTTGAGTGAG | AAGCAGTGTG | TGCTCATCTG | TTCAACCCTG | 9780
| GTGTCTAGAG | ATC | | | | | 9793

(2) INFORMATION FOR SEQ ID NO:57:

(i) SEQUENCE CHARACTERISTICS:
        (A) LENGTH: 1733 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

| | | | | | |
|---|---|---|---|---|---|
| AAACCTCCGA | CGCAACGGGC | TCGGCTTAGC | GGAGTGCACC | TGCTAAGAGG | CGAGAGGAAC | 60
| TCACAAGAGG | GTGAGTAAAT | TTGCTGGCGG | TGGCCAGACC | TAGGGGAAGG | GCGAAGTCCC | 120
| TAGGGGAGGA | AGATGGGTGC | GAGAGCGTCT | GTGTTGACAG | GGAGTAAATT | GGATGCATGG | 180
| GAACGAATTA | GGTTAAGGCC | AGGATCTAAA | AAGGCATATA | GGCTAAAACA | TTTAGTATGG | 240
| GCAAGCAGGG | AGCTGGAAAG | ATACGCATGT | AATCCTGGTC | TATTAGAAAC | TGCAGAAGGT | 300
| ACTGAGCAAC | TGCTACAGCA | GTTAGAGCCA | GCTCTCAAGA | CAGGGTCAGA | GGACCTGAAA | 360
| TCTCTCTGGA | ACGCAATAGC | AGTACTCTGG | TGCGTTCACA | ACAGATTTGA | CATCCGAGAT | 420
| ACACAGCAGG | CAATACAAAA | GTTAAGGAA | GTAATGGCAA | GCAGGAAGTC | TGCAGAGGCC | 480
| GCTAAGGAAG | AAACAAGCCC | TAGGCAGACA | AGTCAAAATT | ACCCTATAGT | AACAAATGCA | 540
| CAGGGACAAA | TGGTACATCA | AGCCATCTCC | CCCAGGACTT | TAAATGCATG | GGTAAAGGCA | 600
| GTAGAAGAGA | AGGCCTTTAA | CCCTGAAATT | ATTCCTATGT | TTATGGCATT | ATCAGAAGGG | 660

| | | | | | | |
|---|---|---|---|---|---|---|
| GCTGTCCCCT | ATGATATCAA | TACCATGCTG | AATGCCATAG | GGGGACACCA | AGGGGCTTTA | 720 |
| CAAGTGTTGA | AGGAAGTAAT | CAATGAGGAA | GCAGCAGAAT | GGGATAGAAC | TCATCCACCA | 780 |
| GCAATGGGGC | CGTTACCACC | AGGGCAGATA | AGGGAACCAA | CAGGAAGTGA | CATTGCTGGA | 840 |
| ACAACTAGCA | CACAGCAAGA | GCAAATTATA | TGGACTACTA | GAGGGCTAA | CTCTATCCCA | 900 |
| GTAGGAGACA | TCTATAGAAA | ATGGATAGTG | CTAGGACTAA | ACAAAATGGT | AAAAATGTAC | 960 |
| AGTCCAGTGA | GCATCTTAGA | TATTAGGCAG | GGACCAAAAG | AACCATTCAG | AGATTATGTA | 1020 |
| GATCGGTTTT | ACAAAACATT | AAGAGCTGAG | CAAGCTACTC | AAGAAGTAAA | GAATTGGATG | 1080 |
| ACAGAAACCT | TGCTTGTTCA | GAATTCAAAC | CCAGATTGTA | AACAAATTCT | GAAAGCATTA | 1140 |
| GGACCAGAAG | CTACTTTAGA | AGAAATGATG | GTAGCCTGTC | AAGGAGTAGG | AGGGCCAACT | 1200 |
| CACAAGGCAA | AAATACTAGC | AGAAGCAATG | GCTTCTGCCC | AGCAAGATTT | AAAAGGAGGA | 1260 |
| TACACAGCAG | TATTCATGCA | AAGAGGGCAG | AATCCAAATA | GAAAAGGGCC | CATAAAATGC | 1320 |
| TTCAATTGTG | GAAAAGAGGG | ACATATAGCA | AAAAACTGTC | GAGCACCTAG | AAAAAGGGGT | 1380 |
| TGCTGGAAAT | GTGGACAGGA | AGGTCACCAA | ATGAAAGATT | GCAAAAATGG | AAGACAGGCA | 1440 |
| AATTTTTTAG | GGAAGTACTG | GCCTCCGGGG | GGCACGAGGC | CAGGCAATTA | TGTGCAGAAA | 1500 |
| CAAGTGTCCC | CATCAGCCCC | ACCAATGGAG | GAGGCAGTGA | AGGAACAAGA | GAATCAGAGT | 1560 |
| CAGAAGGGGG | ATCAGGAAGA | GCTGTACCCA | TTTGCCTCCC | TCAAATCCCT | CTTTGGGACA | 1620 |
| GACCAATAGT | CACAGCAAAG | GTTGGGGGTC | ATCTATGTGA | GGCTTTACTG | GATACAGGGG | 1680 |
| CAGATGATAC | AGTATTAAAT | AACATACAAT | TAGAAGGAAG | ATGGACACCA | AAA | 1733 |

( 2 ) INFORMATION FOR SEQ ID NO:58:

( i ) SEQUENCE CHARACTERISTICS:
    ( A ) LENGTH: 1733 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:58:

| | | | | | | |
|---|---|---|---|---|---|---|
| AAACCTCCAA | CGCAACGGGC | TCGGCTTAGC | GGAGTGCACC | TGCTAAGAGG | CGAGAGGAAC | 60 |
| TCACAAGAGG | GTGAGTAAAT | TTGCTGGCGG | TGGCCAGACC | TAGGGGAAGG | GCGAAGTCCC | 120 |
| TAGGGGAGGA | AGATGGGTGC | GAGACGGTCT | GTGTTGACAG | GGAGTAAATT | GGATGCATGG | 180 |
| GAACGAATTA | GGTTAAGGCC | AGGATCTAAA | AAGGCATATA | GGCTAAAACA | TTTAGTATGG | 240 |
| GCAAGCAGGG | AGCTGGAAAG | ATACGCATAT | AATCCTGGTC | TACTAGAAAC | TGCAGAAGGT | 300 |
| ACTGAACAAC | TGCTACAGCA | GTTAGAGCCA | GCTCTCAAGA | CAGGGTCAGA | GGACCTGAAA | 360 |
| TCCCTCTGGA | ACGCAATAGC | AGTACTCTGG | TGCGTTCACA | ACAGATTTGA | CATCCGAGAT | 420 |
| ACACAGCAGG | CAATACAAAA | GTTAAGGAA | GTAATGGCAA | GCAGGAAGTC | TGCAGAGGCC | 480 |
| GCTAAGGAAG | AAACAAGCTC | AAGGCAGGCA | AGTCAAAATT | ACCCTATAGT | AACAAATGCA | 540 |
| CAGGGACAAA | TGGTACATCA | AGCCATATCC | CCTAGGACTT | TAAATGCATG | GGTAAAGGCA | 600 |
| GTAGAAGAAA | AGGCCTTTAA | CCCTGAAATT | ATTCCTATGT | TTATGGCATT | ATCAGAAGGG | 660 |
| GCTGTCCCCT | ATGATATCAA | TACCATGCTG | AATGCCATAG | GGGGACACCA | AGGGGCTTTA | 720 |
| CAAGTGTTGA | AGGAAGTAAT | CAATGAGGAA | GCAGCAGATT | GGGATAGAAC | TCATCCACCA | 780 |
| GCAATGGGGC | CGTTACCACC | AGGGCAGATA | AGGGAACCAA | CAGGAAGTGA | CATTGCTGGA | 840 |
| ACAACTAGCA | CACAGCAAGA | GCAAATTATA | TGGACTACTA | GAGGGCTAA | CTCTATCCCA | 900 |
| GTAGGAGACA | TCTATAGAAA | ATGGATAGTG | TTAGGACTAA | ACAAAATGGT | AAAAATGTAC | 960 |

| | | | | | | | |
|---|---|---|---|---|---|---|---|
| AGTCCAGTGA | GCATCTTAGA | TATTAGGCAG | GGACCAAAAG | AACCATTCAG | AGATTATGTA | | 1020 |
| GATCGGTTTT | ACAAAACATT | AAGAGCTGAG | CAAGCTACTC | AAGAAGTAAA | GAATTGGATG | | 1080 |
| ACAGAAACCC | TCGTTGTTCA | GAATTCAAAC | CCAGATTGTA | AACAAATTCT | GAAAGCATTA | | 1140 |
| GGACCAGGAG | CTACTTTAGA | AGAAATGATG | GTAGCCTGTC | AAGGAGTAGG | AGGGCCAACT | | 1200 |
| CACAAGGCAA | AAATACTAGC | AGAAGCAATG | GCTTCTGCCC | AGCAAGATTT | AAAGGGAGGA | | 1260 |
| TACACAGCAG | TATTCATGCA | AAGAGGGCAG | AATCCAAATA | GAAAAGGGCC | TATAAAATGT | | 1320 |
| TTCAATTGTG | GAAAAGAGGG | ACATATAGCA | AAAAACTGTC | GAGCACCTAG | AAGAAGGGGT | | 1380 |
| TACTGGAAAT | GTGGACAGGA | AGGTCACCAA | ATGAAAGATT | GCAAAAATGG | AAGACAGGCT | | 1440 |
| ATTTTTTTAG | GGAAGTACTG | GCCTCCGGGG | GGCACGAGGC | CAGCCAATTA | TGTGCAGAAA | | 1500 |
| CAAGTGTCCC | CATCAGCCCC | ACCAATGGAG | GAGGCAGTGA | AGGAACAAGA | GAATCAGAAT | | 1560 |
| CAAAAGGGGG | ATCAGGAAGA | GCTGTACCCA | TTTGCCTCCC | TCAAATCCCT | CTTTGGGACA | | 1620 |
| GACCAATAGT | CACAGCAAAG | GTTGGGGGCC | ATCTATGTGA | GGCTTTACTG | GATACAGGGG | | 1680 |
| CAGATGATAC | AGTATTAAAT | AACATACAAT | TAGAAGGAAG | ATGGACACCC | AAA | | 1733 |

(2) INFORMATION FOR SEQ ID NO:59:

(i) SEQUENCE CHARACTERISTICS:
        (A) LENGTH: 498 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:59:

```
Met Gly Ala Arg Ala Ser Val Leu Thr Gly Ser Lys Leu Asp Ala Trp
 1               5                  10                  15
Glu Arg Ile Arg Leu Arg Pro Gly Ser Lys Lys Ala Tyr Arg Leu Lys
             20                  25                  30
His Leu Val Trp Ala Ser Arg Glu Leu Glu Arg Tyr Ala Cys Asn Pro
         35                  40                  45
Gly Leu Leu Glu Thr Ala Glu Gly Thr Glu Gln Leu Leu Gln Gln Leu
     50                  55                  60
Glu Pro Ala Leu Lys Thr Gly Ser Glu Asp Leu Lys Ser Leu Trp Asn
 65                  70                  75                  80
Ala Ile Ala Val Leu Trp Cys Val His Asn Arg Phe Asp Ile Arg Asp
                 85                  90                  95
Thr Gln Gln Ala Ile Gln Lys Leu Lys Glu Val Met Ala Ser Arg Lys
            100                 105                 110
Ser Ala Glu Ala Ala Lys Glu Glu Thr Ser Pro Arg Gln Thr Ser Gln
        115                 120                 125
Asn Tyr Pro Ile Val Thr Asn Ala Gln Gly Gln Met Val His Gln Ala
    130                 135                 140
Ile Ser Pro Arg Thr Leu Asn Ala Trp Val Lys Ala Val Glu Glu Lys
145                 150                 155                 160
Ala Phe Asn Pro Glu Ile Ile Pro Met Phe Met Ala Leu Ser Glu Gly
                165                 170                 175
Ala Val Pro Tyr Asp Ile Asn Thr Met Leu Asn Ala Ile Gly Gly His
            180                 185                 190
Gln Gly Ala Leu Gln Val Leu Lys Glu Val Ile Asn Glu Glu Ala Ala
        195                 200                 205
```

| Glu | Trp | Asp | Arg | Thr | His | Pro | Pro | Ala | Met | Gly | Pro | Leu | Pro | Pro | Gly |
| | 210 | | | | | 215 | | | | | 220 | | | | |
| Gln | Ile | Arg | Glu | Pro | Thr | Gly | Ser | Asp | Ile | Ala | Gly | Thr | Thr | Ser | Thr |
| 225 | | | | | 230 | | | | | 235 | | | | | 240 |
| Gln | Gln | Glu | Gln | Ile | Ile | Trp | Thr | Thr | Arg | Gly | Ala | Asn | Ser | Ile | Pro |
| | | | | 245 | | | | | 250 | | | | | 255 | |
| Val | Gly | Asp | Ile | Tyr | Arg | Lys | Trp | Ile | Val | Leu | Gly | Leu | Asn | Lys | Met |
| | | | 260 | | | | | 265 | | | | | 270 | | |
| Val | Lys | Met | Tyr | Ser | Pro | Val | Ser | Ile | Leu | Asp | Ile | Arg | Gln | Gly | Pro |
| | | 275 | | | | | 280 | | | | | 285 | | | |
| Lys | Glu | Pro | Phe | Arg | Asp | Tyr | Val | Asp | Arg | Phe | Tyr | Lys | Thr | Leu | Arg |
| | 290 | | | | | 295 | | | | | 300 | | | | |
| Ala | Glu | Gln | Ala | Thr | Gln | Glu | Val | Lys | Asn | Trp | Met | Thr | Glu | Thr | Leu |
| 305 | | | | | 310 | | | | | 315 | | | | | 320 |
| Leu | Val | Gln | Asn | Ser | Asn | Pro | Asp | Cys | Lys | Gln | Ile | Leu | Lys | Ala | Leu |
| | | | | 325 | | | | | 330 | | | | | 335 | |
| Gly | Pro | Glu | Ala | Thr | Leu | Glu | Glu | Met | Met | Val | Ala | Cys | Gln | Gly | Val |
| | | | 340 | | | | | 345 | | | | | 350 | | |
| Gly | Gly | Pro | Thr | His | Lys | Ala | Lys | Ile | Leu | Ala | Glu | Ala | Met | Ala | Ser |
| | | 355 | | | | | 360 | | | | | 365 | | | |
| Ala | Gln | Gln | Asp | Leu | Lys | Gly | Gly | Tyr | Thr | Ala | Val | Phe | Met | Gln | Arg |
| | 370 | | | | | 375 | | | | | 380 | | | | |
| Gly | Gln | Asn | Pro | Asn | Arg | Lys | Gly | Pro | Ile | Lys | Cys | Phe | Asn | Cys | Gly |
| 385 | | | | | 390 | | | | | 395 | | | | | 400 |
| Lys | Glu | Gly | His | Ile | Ala | Lys | Asn | Cys | Arg | Ala | Pro | Arg | Lys | Arg | Gly |
| | | | | 405 | | | | | 410 | | | | | 415 | |
| Cys | Trp | Lys | Cys | Gly | Gln | Glu | Gly | His | Gln | Met | Lys | Asp | Cys | Lys | Asn |
| | | | 420 | | | | | 425 | | | | | 430 | | |
| Gly | Arg | Gln | Ala | Asn | Phe | Leu | Gly | Lys | Tyr | Trp | Pro | Pro | Gly | Gly | Thr |
| | | | 435 | | | | | 440 | | | | | 445 | | |
| Arg | Pro | Gly | Asn | Tyr | Val | Gln | Lys | Gln | Val | Ser | Pro | Ser | Ala | Pro | Pro |
| | 450 | | | | | 455 | | | | | 460 | | | | |
| Met | Glu | Glu | Ala | Val | Lys | Glu | Gln | Glu | Asn | Gln | Ser | Gln | Lys | Gly | Asp |
| 465 | | | | | 470 | | | | | 475 | | | | | 480 |
| Gln | Glu | Glu | Leu | Tyr | Pro | Phe | Ala | Ser | Leu | Lys | Ser | Leu | Phe | Gly | Thr |
| | | | | 485 | | | | | 490 | | | | | 495 | |
| Asp | Gln | | | | | | | | | | | | | | |

( 2 ) INFORMATION FOR SEQ ID NO:60:

( i ) SEQUENCE CHARACTERISTICS:
        ( A ) LENGTH: 498 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:60:

| Met | Gly | Ala | Arg | Arg | Ser | Val | Leu | Thr | Gly | Ser | Lys | Leu | Asp | Ala | Trp |
| 1 | | | | 5 | | | | | 10 | | | | | 15 | |
| Glu | Arg | Ile | Arg | Leu | Arg | Pro | Gly | Ser | Lys | Lys | Ala | Tyr | Arg | Leu | Lys |
| | | | | 20 | | | | | 25 | | | | | 30 | |
| His | Leu | Val | Trp | Ala | Ser | Arg | Glu | Leu | Glu | Arg | Tyr | Ala | Tyr | Asn | Pro |
| | | | | 35 | | | | | 40 | | | | | 45 | |
| Gly | Leu | Leu | Glu | Thr | Ala | Glu | Gly | Thr | Glu | Gln | Leu | Leu | Gln | Gln | Leu |

```
                    50                          55                            60
Glu  Pro  Ala  Leu  Lys  Thr  Gly  Ser  Glu  Asp  Leu  Lys  Ser  Leu  Trp  Asn
 65                      70                       75                        80

Ala  Ile  Ala  Val  Leu  Trp  Cys  Val  His  Asn  Arg  Phe  Asp  Ile  Arg  Asp
                    85                       90                       95

Thr  Gln  Gln  Ala  Ile  Gln  Lys  Leu  Lys  Glu  Val  Met  Ala  Ser  Arg  Lys
                   100                  105                      110

Ser  Ala  Glu  Ala  Ala  Lys  Glu  Glu  Thr  Ser  Ser  Thr  Gln  Ala  Ser  Gln
              115                       120                      125

Asn  Tyr  Pro  Ile  Val  Thr  Asn  Ala  Gln  Gly  Gln  Met  Val  His  Gln  Ala
 130                           135                      140

Ile  Ser  Pro  Arg  Thr  Leu  Asn  Ala  Trp  Val  Lys  Ala  Val  Glu  Glu  Lys
 145                     150                      155                       160

Ala  Phe  Asn  Pro  Glu  Ile  Ile  Pro  Met  Phe  Met  Ala  Leu  Ser  Glu  Gly
                    165                       170                       175

Ala  Val  Pro  Tyr  Asp  Ile  Asn  Thr  Met  Leu  Asn  Ala  Ile  Gly  Gly  His
               180                      185                      190

Gln  Gly  Ala  Leu  Gln  Val  Leu  Lys  Glu  Val  Ile  Asn  Glu  Glu  Ala  Ala
          195                      200                      205

Asp  Trp  Asp  Arg  Thr  His  Pro  Pro  Ala  Met  Gly  Pro  Leu  Pro  Pro  Gly
 210                          215                      220

Gln  Ile  Arg  Glu  Pro  Thr  Gly  Ser  Asp  Ile  Ala  Gly  Thr  Thr  Ser  Thr
 225                     230                      235                       240

Gln  Gln  Glu  Gln  Ile  Ile  Trp  Thr  Thr  Arg  Gly  Ala  Asn  Ser  Ile  Pro
                    245                      250                      255

Val  Gly  Asp  Ile  Tyr  Arg  Lys  Trp  Ile  Val  Leu  Gly  Leu  Asn  Lys  Met
              260                      265                      270

Val  Lys  Met  Tyr  Ser  Pro  Val  Ser  Ile  Leu  Asp  Ile  Arg  Gln  Gly  Pro
          275                      280                      285

Lys  Glu  Pro  Phe  Arg  Asp  Tyr  Val  Asp  Arg  Phe  Tyr  Lys  Thr  Leu  Arg
     290                      295                      300

Ala  Glu  Gln  Ala  Thr  Gln  Glu  Val  Lys  Asn  Trp  Met  Thr  Glu  Thr  Leu
 305                     310                      315                       320

Val  Val  Gln  Asn  Ser  Asn  Pro  Asp  Cys  Lys  Gln  Ile  Leu  Lys  Ala  Leu
                    325                      330                      335

Gly  Pro  Gly  Ala  Thr  Leu  Glu  Glu  Met  Met  Val  Ala  Cys  Gln  Gly  Val
               340                      345                      350

Gly  Gly  Pro  Thr  His  Lys  Ala  Lys  Ile  Leu  Ala  Glu  Ala  Met  Ala  Ser
          355                      360                      365

Ala  Gln  Gln  Asp  Leu  Lys  Gly  Gly  Tyr  Thr  Ala  Val  Phe  Met  Gln  Arg
 370                          375                      380

Gly  Gln  Asn  Pro  Asn  Arg  Lys  Gly  Pro  Ile  Lys  Cys  Phe  Asn  Cys  Gly
 385                     390                      395                       400

Lys  Glu  Gly  His  Ile  Ala  Lys  Asn  Cys  Arg  Ala  Pro  Arg  Arg  Arg  Gly
                    405                      410                      415

Tyr  Trp  Lys  Cys  Gly  Gln  Glu  Gly  His  Gln  Met  Lys  Asp  Cys  Lys  Asn
               420                      425                      430

Gly  Arg  Gln  Ala  Asn  Phe  Leu  Gly  Lys  Tyr  Trp  Pro  Pro  Gly  Gly  Thr
          435                      440                      445

Arg  Pro  Ala  Asn  Tyr  Val  Gln  Lys  Gln  Val  Ser  Pro  Ser  Ala  Pro  Pro
 450                          455                      460

Met  Glu  Glu  Ala  Val  Lys  Glu  Gln  Glu  Asn  Gln  Asn  Gln  Lys  Gly  Asp
 465                     470                      475                       480
```

-continued

```
Gln Glu Glu Leu Tyr Pro Phe Ala Ser Leu Lys Ser Leu Phe Gly Thr
              485                 490                 495
Asp Gln
```

(2) INFORMATION FOR SEQ ID NO:61:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (xi) SEQUENCE DESCRIPTION: SEQ ID NO:61:

```
Arg Ile Leu Ala Val Glu Arg Tyr Leu Lys Asp Gln Gln Leu Leu Gly
 1               5                  10                  15
Ile Trp Gly Cys Ser Gly Lys Leu Ile Cys Thr Thr Ala Val Pro Trp
                20                  25                  30
Asn Ala Ser
         35
```

(2) INFORMATION FOR SEQ ID NO:62:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (xi) SEQUENCE DESCRIPTION: SEQ ID NO:62:

```
Arg Leu Gln Ala Leu Glu Thr Leu Ile Gln Asn Gln Gln Arg Leu Asn
 1               5                  10                  15
Leu Trp Gly Cys Lys Gly Lys Leu Ile Cys Tyr Thr Ser Val Lys Trp
                20                  25                  30
Asn Thr Ser
         35
```

(2) INFORMATION FOR SEQ ID NO:63:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (xi) SEQUENCE DESCRIPTION: SEQ ID NO:63:

```
Trp Gly Ile Arg Gln Leu Arg Ala Arg Leu Gln Ala Leu Glu Thr Leu
 1               5                  10                  15
Ile Gln Asn Gln Gln Arg Leu Asn Leu
                20                  25
```

RETROVIRUS FROM THE HIV GROUP AND ITS USE

This is a division of application Ser. No. 08/132,653, filed Oct. 5, 1993 now abandoned.

The present invention relates to a novel retrovirus from the HIV group, as well as to variants or parts thereof which contain the essential properties of the virus. A process is described for culturing the retrovirus. The invention furthermore relates to the isolation of this retrovirus and to use of the virus, its parts or extracts for medicinal purposes, for diagnostics and in the preparation of vaccines.

Retroviruses which belong to the so-called HIV group lead in humans who are infected by them to disease manifestations which are summarized under the collective term immunodeficiency or AIDS (acquired immune deficiency syndrome).

Epidemiological studies verify that the human immunodeficiency virus (HIV) represents the etiological agent in the vast majority of AIDS (acquired immune deficiency syndrome) cases. A retrovirus which was isolated from a patient and characterized in 1983 received. The designation HIV-1 (Barré-Sinoussi, F. et al., Science 220, 868–871 [1983]). A variant of HIV-1 is described in WO 86/02383.

A second group of human immunodeficiency viruses was identified in 1985 in West Africa (Clavel, F. et al., Science 233, 343–346 [1986]) and designated human immunodeficiency virus type 2 (HIV-2) (EP-A-0 239 425). While HIV-2 retroviruses clearly differ from HIV-1, they do exhibit affinity with simian immunodeficiency viruses (SIV-2). Like HIV-1, HIV-2 also leads to AIDS symptomatology.

A further variant of an immunodeficiency retrovirus is described in EP-A-0 345 375 and designated there as HIV-3 retrovirus (ANT 70).

The isolation of a further, variant, immunodeficiency virus is also described in Lancet Vol. 340, Sept. 1992, pp. 681–682.

It is characteristic of human immunodeficiency viruses that they exhibit a high degree of variability, which significantly complicates the comparability of the different isolates. For example, when diverse HIV-1 isolates are compared, high degrees of variability are found in some regions of the genome while other regions are comparatively well conserved (Benn, S. et al., Science 230, 949–951[1985]). It was also possible to observe an appreciably greater degree of polymorphism in the case of HIV-2 (Clavel, F. et al., Nature 324, 691–695 [1986]). The greatest degree of genetic stability is possessed by regions in the gag and pol genes which encode proteins which are essential for structural and enzymic purposes; some regions in the env gene, and the genes (vif, vpr, tat, rev and nef) encoding regulatory proteins, exhibit a high degree of variability. In addition to this, it was possible to demonstrate that antisera against HIV-1 also crossreact with gag and pol gene products from HIV-2 even though there was only a small degree of sequence homology. Little hybridization of significance likewise took place between these two viruses unless conditions of very low stringency were used (Clavel, F. et al., Nature 324, 691–695 [1986]).

Owing to the wide distribution of retroviruses from the HIV group and to the fact that a period of a few to many years (2–20) exists between the time of infection and the time at which unambiguous symptoms of pathological changes are recognizable, it is of great importance from the epidemiological point of view to determine infection with retroviruses of the HIV group at as early a stage as possible and, above all, in a reliable manner. This is not only of importance when diagnosing patients who exhibit signs of immunodeficiency, but also when monitoring blood donors. It has emerged that, when retroviruses of the HIV-1 or HIV-2 type, or components thereof, are used in detection systems, antibodies can either not be detected or only detected weakly in many sera even though signs of immunodeficiency are present in the patients from which the sera are derived. In certain cases, such detection is possible using the retrovirus from the HIV group according to the invention.

This patent describes the isolation and characterization of a novel human immunodeficiency virus, designated below as MVP-5180/91, (SEQ ID NO:56) which was isolated from the peripheral lymphocytes of a female patient from the Cameroons who was 34 years old in 1991 and who exhibited signs of immunodeficiency. From the point of view of geography, this retrovirus originates from a region in Africa which is located between West Africa, where there is endemic infection with HIV-2 and HIV-1 viruses, and Eastern Central Africa, where it is almost exclusively HIV-1 which is disseminated. Consequently, the present invention relates to a novel retrovirus, designated MVP-5180/91 (SEQ ID NO:56, of the HIV group and its variants, to DNA sequences, amino acid sequences and constituent sequences derived therefrom, and to test kits containing the latter. The retrovirus MVP-5180/91 (SEQ ID NO:56) has been deposited with the European Collection of Animal Cell Cultures (ECACC) PHLS Centre for Applied Microbiology & Research, Porton Down, Salisbury, Wilts. SP4 OJG, U.K., on Sept. 23, 1992, PHLS Centre for Applied Microbiology & Research, Porton Down, Salisbury Wilts. SP4 OJG, United Kingdom, on Sept. 23, 1992 under ECACC Accession No. V 920 92 318 in accordance with the stipulations of the Budapest Treaty.

As do HIV-1 and HIV-2, MVP-5180/91 (SEQ ID NO:56) according to the invention grows in the following cell lines: HUT 78, Jurkat cells, C8166 cells and MT-2 cells. The isolation and propagation of viruses is described in detail in the book "Viral Quantitation in HIV Infection, Editor Jean-Marie Andrieu, John Libbey Eurotext, 1991". The procedural methods described in that publication are by reference made a subject of the disclosure of the present application.

In addition to this, the virus according to the invention possesses a reverse transcriptase which is magnesium-dependent but not manganese-dependent. This represents a further property possessed in common with the HIV-1 and HIV-2 viruses.

In order to provide a better understanding of the differences between the MVP-5180/91 (SEQ ID NO:56) virus according to the invention and the HIV-1 and HIV-2 retroviruses, the construction of the retroviruses which cause immunodeficiency will first of all be explained in brief. Within the virus, the RNA is located in a conical core which is assembled from protein subunits which carry the designation p 24 (p for protein). This inner core is surrounded by a protein coat, which is constructed from protein p 17 (outer core), and by a glycoprotein coat which, in addition to lipids, which originate from the host cell, contains the transmembrane protein gp 41 and the coat protein 120 (gp 120). This gp 120 can then bind to the CD-4 receptors of the host cells.

BRIEF DESCRIPTION OF THE DRAWINGS

FIG. 4 depicts the almost complete DNA sequence of the retrovirus MVP-5180/91.

FIG. 6 depicts a comparison of the sequence in FIG. 4 to the sequence obtained using the PCR amplification techniques depicted in FIG. 5.

FIG. 7 depicts a comparison of the amino acid sequences of the gag protein deduced from the sequence of FIG. 4 with the gag protein sequence obtained using the PCR amplification techniques depicted in FIG. 5.

DETAILED DESCRIPTION OF THE INVENTION

Figure 1:
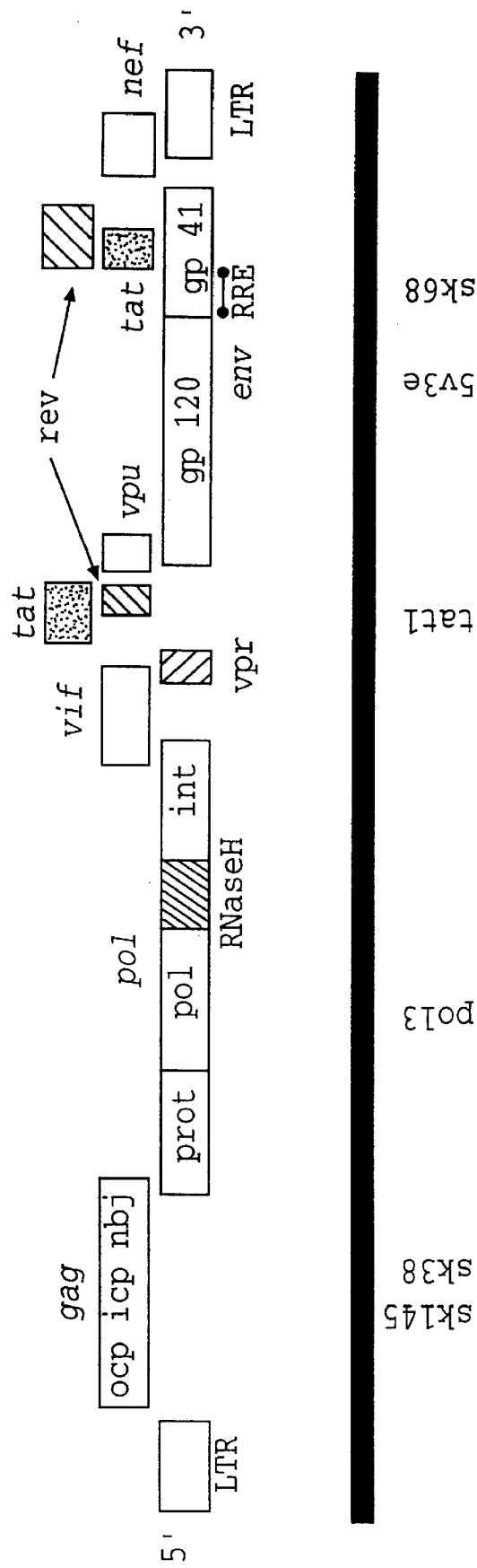
FIG. 1 depicts the arrangement of the genome of retroviruses of the HIV type.

As far as is known, the RNA of HIV viruses—portrayed in a simplified manner—possesses the following gene regions: so-called long terminal repeats (LTR) at each end, together with the following gene regions: gag, pol, env and nef. The gag gene encodes, inter alia, the core proteins, p 24 and p 17, the pol gene encodes, inter alia, the reverse transcriptase, the RNAse H and the integrase, while the env gene encodes the gp 41 and gp 120 glycoproteins of the virus coat. The nef gene encodes a protein having a regulatory function. The arrangement of the genome of retroviruses of the HIV type is shown diagrammatically in FIG. 1.

Figure 2:
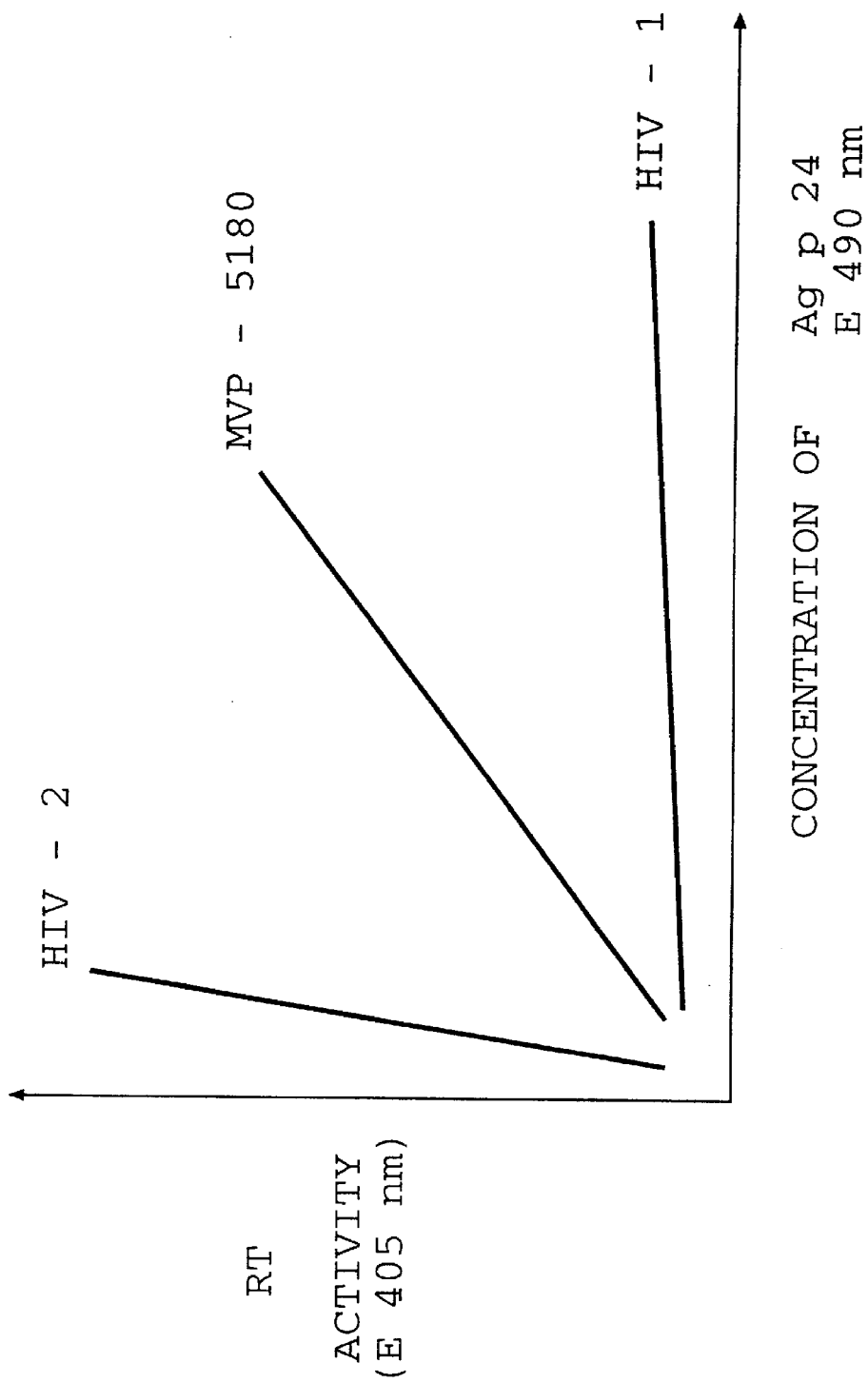
FIG. 2 is a graph depicting the binding affinity for the monoclonal antibody p24 in relation to the content of reverse transcriptase for the retroviruses HIV-1, HIV-2, and MVP-5180/91.
Figure 3:
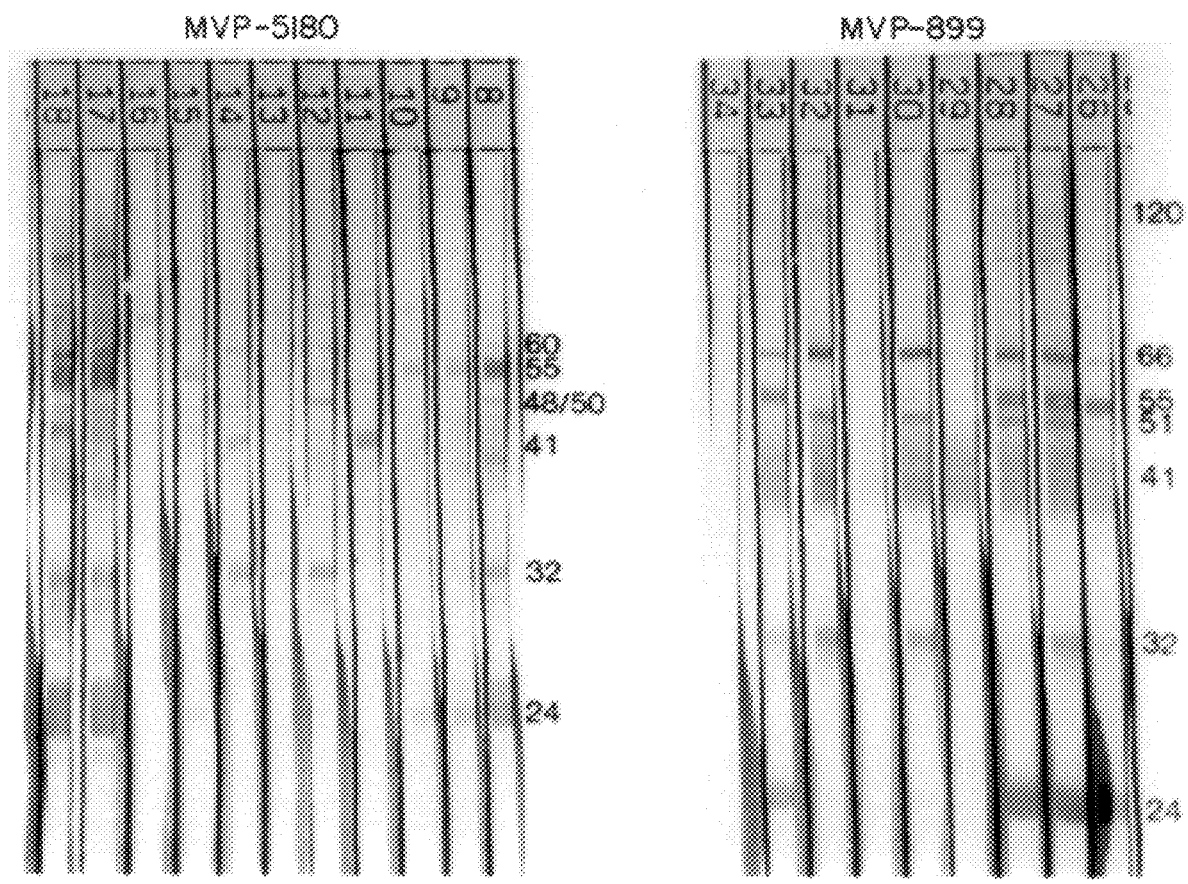
FIG. 3 depicts a western blot of MVP-5180/91 and HIV-1, isolated from German patients.

The HIV-1 and HIV-2 retroviruses can be distinguished, inter alia, by testing viral antigen using a monoclonal antibody which is commercially available from Abbott (HIVAG-1 monoclonal) in the form of a test kit and is directed against (HIV-1) p 24. It is known that the content of reverse transcriptase is roughly the same in the HIV-1 and HIV-2 virus types. If, therefore, the extinction (E 490 nm) obtained in dilutions of the disrupted viruses by means of the antigen-antibody reaction is plotted against the activity of reverse transcriptase, a series of graphs is obtained corresponding roughly to that in FIG. 2. In this context, it is observed that, in the case of HIV-1, the monoclonal antibody employed has a very high binding affinity for p 24 in relation to the content of reverse transcriptase. By contrast, the monoclonal antibody employed has only a very low binding affinity for p 24 in the case of HIV-2, once again in relation to the content of reverse transcriptase. If these measurements are carried out on MVP-5180/91 (SEQ ID NO:56), the curve is then located almost precisely in the centre between the curves for HIV-1 and HIV-2, i.e. The binding affinity of the monoclonal antibody for MVP-5180/91 p 24 is reduced as compared with the case of HIV-1. FIG. 2 shows this relationship diagrammatically, with RT denoting reverse transcriptase, and the protein p 24, against which is directed the monoclonal antibody which is present in the test kit which can be purchased from Abbott, being employed as the antigen (Ag).

The so-called PCR (polymerase chain reaction) system has proved to have a multiplicity of uses in genetic manipulation, and the components which are required for implementing the process can be purchased. Using this process, it is possible to amplify DNA sequences if regions of the sequence to be amplified are known. Short, complementary DNA fragments (oligonucleotides=primers) have then to be synthesized which anneal to a short region of the nucleic acid sequence to be amplified. For carrying out the test, HIV nucleic acids are introduced together with the primers into a reaction mixture which additionally contains a polymerase and nucleotide triphosphates. The polymerization (DNA synthesis) is carried out for a given time and the nucleic acid strands are then separated by heating. After cooling, the polymerization then proceeds once more. If, therefore, the retrovirus according to the invention is an HIV-1 or HIV-2 virus, it should be possible to amplify the nucleic acid using primers which are conserved within the known sequences of the HIV-1 and HIV-2 viruses. Some primers of this type have previously been described (Lauré, F. et al., Lancet ii, (1988) 538–541 for pol 3 and pol 4, and Ou C.Y. et al., Science 239 (1988) 295–297 for sk 38/39 and sk 68/69).

It was discovered that use of particular primer pairs having the following sequence:
gaga (SEQ ID NO:1): CTACT AGTAC CCTTC AGG
gagb (SEQ ID NO:2): CGGTC TACAT AGTCT CTAAA G
sk38 (SEQ ID NO:3): CCACC TATCC CAGTA GGAGA A
sk39 (SEQ ID NO:4): CCTTT GGTCC TTGTC TTATG TCCAG AATGC
or
pol3 (SEQ ID NO:5): TGGGA AGTTC AATTA GGAAT ACCAC
pol4 (SEQ ID NO:6): CCTAC ATAGA AATCA TCCAT GTATT G
pol3n (SEQ ID NO:7): TGGAT GTGGG TGATG CATA
pol4n (SEQ ID NO:8): AGCAC ATTGT ACTGA TATCT A
and
SK145 (SEQ ID NO:9): AGTGG GGGGA CATCA AGCAG CC
SK150 (SEQ ID NO:10): TGCTA TGTCA CTTCC CCTTG GT
145-P (SEQ ID NO:11): CCATG CAAAT GTTAA AAGAG AC
150-P (SEQ ID NO:12): GGCCT GGTGC AATAG GCCC
or a combination of pol 3 and pol 4 with
UNI-1 (SEQ ID NO:13): GTGCT TCCAC AGGGA TGGAA
UNI-2 (SEQ ID NO:14): ATCAT CCATG TATTG ATA
(Donehower L. A. et al. (1990) J. Virol. Methods 28, 33–46) and employing PCR with nested primers, led to weak amplifications of the MVP-5180/91 DNA (SEQ ID NO:56).

No amplification, or only weak amplification as compared with HIV-1, possibly attributable to impurities, was obtained with the following primer sequences:
tat 1 (SEQ ID NO:15) AATGG AGCCA GTAGA TCCTA
tat 2 (SEQ ID NO:16) TGTCT CCGCT TCTTC CTGCC
tat 1P (SEQ ID NO:17) GAGCC CTGGA AGCAT CCAGG
tat 2P (SEQ ID NO:18) GGAGA TGCCT AAGGC TTTTG
enva (SEQ ID NO:19): TGTTC CTTGG GTTCT TG
envb (SEQ ID NO:20): GAGTT TTCCA GAGCA ACCCC
sk68 (SEQ ID NO:21): AGCAG CAGGA AGCAC TATGG
sk69 (SEQ ID NO:22): GCCCC AGACT GTGAG TTGCA ACAG
5v3e (SEQ ID NO:23): GCACA GTACA ATGTA CACAT GG
3v3e (SEQ ID NO:24): CAGTA GAAAA ATTCC CCTCC AG
5v3degi (SEQ ID NO:25): TCAGG ATCCA TGGGC AGTCT AGCAG AAGAA G
3v3degi (SEQ ID NO:26): ATGCT CGAGA ACTGC AGCAT CGAT CTGGG TCCCC TCCTG AG
3v3longdegi (SEQ ID NO:27): CGAGA ACTGC AGCAT CGATG CTGCT CCCAA GAACC CAAGG
3v3longext (SEQ ID NO:28): GGAGC TGCTT GATGC CCCAG A
gagdi (SEQ ID NO:29): TGATG ACAGC ATGTC AGGGA GT pol e (SEQ ID NO:30): GCTGA CATTT ATCAC AGCTG GCTAC Amplifications which were weak as compared with those for HIV-1, but nevertheless of the same intensity as those for the HIV-2 isolate (MVP-11971/87) employed, were obtained with gag c (SEQ ID NO:31): TATCA CCTAG AACTT TAAAT GCATG GG gag d (SEQ ID NO:32): AGTCC CTGAC ATGCT GTCAT CA env c (SEQ ID NO:33): GTGGA GGGGA ATTTT TCTAC TG env d (SEQ ID NO:34): CCTGC TGCTC CCAAG AACCC AAGG The so-called Western blot (immunoblot) is a common method for detecting HIV antibodies. In this method, the viral proteins are fractionated by gel electrophoresis and then transferred to a membrane. The membranes provided with the transferred proteins are then brought into contact with sera from the patients to be investigated. If antibodies against the viral proteins are present, these antibodies will bind to the proteins. After the membranes have been washed, only antibodies which are specific for the viral proteins will remain. The antibodies are then rendered visible using antiantibodies which, as a rule, are coupled to an enzyme which catalyzes a color reaction. In this way, the bands of the viral proteins can be rendered visible.

The virus MVP-5180/91 (SEQ ID NO:56) according to the invention exhibits two significant and important differences from the HIV-1 and HIV-2 viruses in a Western blot. HIV-1 regularly shows a strong band, which is attributable to protein p 24, and a very weak band, which is often scarcely visible and which is attributable to protein p 23. HIV-2 exhibits a strong band, which is attributable to protein p 25, and sometimes a weak band, which is attributable to protein p 23. In contrast to this, the MVP-5180/91 (SEQ ID NO:56) virus according to the invention exhibits two bands of approximately equal strength, corresponding to proteins p 24 and p 25.

A further significant difference exists in the bands which are attributable to reverse transcriptase. HIV-1 shows one band (p 53) which corresponds to reverse transcriptase and one band (p 66) which corresponds to reverse transcriptase bound to RNAse H. In the case of HIV-2, the reverse transcriptase corresponds to protein p 55 and, if it is bound to RNAse H, to protein p 68. By contrast, MPV-5180/91 (SEQ ID NO:56) according to the invention exhibits one band at protein p 48, which corresponds to reverse transcriptase, and one band, at protein p 60, which corresponds to reverse transcriptase bound to RNAse H. It can be deduced from these results that the reverse transcriptase of MVP-5180/91 (SEQ ID NO:56) has a molecular weight which is roughly between 3 and 7 kilodaltons less than that of the reverse transcriptases of HIV-1 and HIV-2. The reverse transcriptase of MVP-5180 consequently has a molecular weight which is roughly between 4,500 daltons and 5,500 daltons less than that of the reverse transcriptase of HIV-1 or HIV-2.

It was discovered that anti-env antibodies could only be detected weakly in the sera of German patients exhibiting signs of immunodeficiency when the MVP-5180/91 (SEQ ID NO:56) virus according to the invention was used, whereas the sera reacted strongly if an HIV-1 virus was used instead of the virus according to the invention. This stronger detection reaction was located in the gp 41 protein, in particular. In the experiments, serum panels were compared which on the one hand derived from German patients and on the other from African patients showing signs of immune deficiency.

The abovementioned characteristics are indicative of those virus variants which correspond to MVP-5180/91 (SEQ ID NO:56) according to the invention. Therefore, the virus according to the invention, or variants thereof, can be obtained by isolating immunodeficiency viruses from heparinized donor blood derived from persons who exhibit signs of immune deficiency and who preferably originate from Africa.

Since the virus possessing the abovementioned properties has been isolated, the cloning of a cDNA can be carried out in the following manner: the virus is precipitated from an appropriately large quantity of culture (about 1 1) and then taken up in phosphate-buffered sodium chloride solution. It is then pelleted through a (20% strength) sucrose cushion. The virus pellet can be suspended in 6M guanidinium chloride in 20 mM dithiothreitol and 0.5% Nonidet P 40. CsCl is added to bring its concentration to 2 molar and the solution containing the disrupted virus is transferred to a cesium chloride cushion. The viral RNA is then pelleted by centrifugation, and subsequently dissolved, extracted with phenol and precipitated with ethanol and lithium chloride. Synthesis of the first cDNA strand is carried out on the viral RNA, or parts thereof, using an oligo(dT) primer. The synthesis can be carried out using a commercially available kit and adding reverse transcriptase. To synthesize the second strand, the RNA strand of the RNA/DNA hybrid is digested with RNase H, and the second strand is then synthesized using *E. coli* DNA polymerase I. Blunt ends can then be produced using T4 DNA polymerase and these ends can be joined to suitable linkers for restriction cleavage sites. Following restriction digestion with the appropriate restriction endonuclease, the cDNA fragment is isolated from an agarose gel and ligated to a vector which has previously been cut in an appropriate manner. The vector containing the cDNA insert can then be used for transforming competent *E. coli* cells. The colonies which are obtained are then transferred to membranes, lysed and denatured, and then finally detected by hybridization nucleic acid labeled with digoxigenin or biotin. Once the corresponding cDNA has been prepared by genetic manipulation, it is possible to isolate the desired DNA fragments originating from the retrovirus. By incorporating these fragments into suitable expression vectors, the desired protein or protein fragment can then be expressed and employed for the diagnostic tests.

As an alternative to the stated method, the immunodeficiency virus can be cloned with the aid of PCR technology, it being possible to use the abovementioned primers.

The similarity between different virus isolates can be expressed by the degree of homology between the nucleic acid or protein sequences. 50% homology means, for example, that 50 out of 100 nucleotides or amino acid positions in the sequences correspond to each other. The homology of proteins is determined by sequence analysis. Homologous DNA sequences can also be identified by the hybridization technique.

In accordance with the invention, a part of the coat protein was initially sequenced and it was ascertained that this sequence possessed only relatively slight homology to the corresponding sequences from viruses of the HIV type. On the basis of a comparison with HIV sequences, which was carried out using data banks, it was established, in relation to the gp 41 region in particular, that the homology was at most 66% (nucleotide sequence).

In addition to this, the region was sequenced which encodes gp 41. This sequence is presented in Tables 1 and 3 Table 1 includes DNA SEQ ID NO:37, DNA SEQ ID NO:38, and amino acid SEQ ID NO:39. Table 3 includes DNA SEQ ID NO:44, DNA SEQ ID NO:45, and amino acid SEQ ID NO:46.

The present invention therefore relates to those viruses which possess an homology of more than 66%, preferably 75% and particularly preferably 85%, to the HIV virus, MVP-5180/91 (SEQ ID NO:56), according to the invention, based on the nucleotide sequence in Table 1 (SEQ ID NO:37; SEQ ID NO:38) and/or in Table 3 (SEQ ID NO:44; SEQ ID NO:45).

Furthermore, the present invention relates to those viruses which possess an homology of more than 66%, preferably 75% and particularly preferably 85%, to partial sequences of the nucleotide sequence presented in Table 3 (SEQ ID NO:44; SEQ ID NO:45), which sequences are at least 50, preferably 100, nucleotides long. This corresponds to a length of the peptides of at least 16, and preferably of at least 33, amino acids.

The sequence of the virus according to the invention differs from that of previously known viruses. The present invention therefore relates to those viruses, and corresponding DNA and amino acid sequences, which correspond to a large extent to the sequence of the virus according to the invention, the degree of deviation being established by the degree of homology. An homology of, for example, more than 85% denotes, therefore, that those sequences are included which have in at least 85 of 100 nucleotides or amino acids the same nucleotides or amino acids, respectively, while the remainder can be different. When establishing homology, the two sequences are compared in such a way that the greatest possible number of nucleotides or amino acids corresponding to each other are placed in congruence.

The (almost) complete sequence, given as the DNA sequence of the virus according to the invention, is reproduced in FIG. 4 and included as DNA SEQ ID NO:56. In this context, the present invention rleates to viruses which possess the sequence according to FIG. 4 (SEQ ID NO:56), and variants thereof which possess a high degree of homology with the sequence of FIG. 4 (SEQ ID NO:56), as well as proteins, polypeptides and oligopeptides derived therefrom which can be used diagnostically or can be employed as vaccines.

Using the isolated sequence as a basis, immunodominant epitopes (peptides) can be designed and synthesized. Since the nucleic acid sequence of the virus is known, the person skilled in the art can derive the amino acid sequence from this known sequence. A constituent region of the amino acid sequence is given in Table 3 (SEQ ID NO:46). The present invention also relates, therefore, to antigens, i.e. proteins, oligopeptides or polypeptides, which can be prepared with the aid of the information disclosed in FIG. 4 (SEQ ID NO:56) and Table 3 (SEQ ID NO:44, SEQ ID NO:45, and SEQ ID NO:46). These antigens, proteins, polypeptides and oligopeptides possess amino acid sequences which can either be derived from FIG. 4 (SEQ ID NO:56) or are given in Table 3 (SEQ ID NO:46). The antigens or peptides can possess relatively short constituent sequences of an amino acid sequence which is reproduced in Table 3 (SEQ ID NO:46) or which can be derived from FIG. 4 (SEQ ID NO:56). This amino acid sequence is at least 6, preferably at least 10 and particularly preferably at least 15, amino acids in length. These peptides can be prepared not only with the aid of recombinant technology but also using synthetic methods. A suitable preparation route is solid-phase synthesis of the Merrifield type. Further description of this technique, and of other processes known to the state of the art, can be found in the literature, e.g. M. Bodansky, et al., Peptide Synthesis, John Wiley & Sons, 2nd Edition 1976.

In the diagnostic tests, a serum sample from the person to be investigated is brought into contact with the protein chains of one or more proteins or glycoproteins (which can be expressed in eukaryotic cell lines), or parts thereof, which originate from MVP-5180/91 (SEQ ID NO:56). Test processes which are preferred include immunofluorescence or immunoenzymatic test processes (e.g. ELISA or immunoblot).

In the immunoenzymatic tests (ELISA), antigen originating from MVP-5180/91 (SEQ ID NO:56) or a variant thereof, for example, can be bound to the walls of microtiter plates. The dosage used in this context depends to an important degree on the test system and the treatment of the microtiter plates. Serum or dilutions of serum deriving from the person to be investigated are then added to the wells of the microtiter plates. After a predetermined incubation time, the plate is washed and specific immunocomplexes are detected by antibodies which bind specifically to human immunoglobulins and which had previously been linked to an enzyme, for example horseradish peroxidase, alkaline phosphatase, etc., or to enzyme-labeled antigen. These enzymes are able to convert a colorless substrate into a strongly colored product, and the presence of specific anti-HIV antibodies can be gathered from the strength of the coloration. A further option for using the virus according to the invention in test systems is its use in Western blots.

Even if the preparation of vaccines against immunodeficiency diseases is proving to be extremely difficult, this virus, too, or parts thereof, i.e. immunodominant epitopes and inducers of cellular immunity, or antigens prepared by genetic manipulation, can still be used for developing and preparing vaccines.

EXAMPLE 1

The immunodeficiency virus according to the invention, MVP-5180/91 (SEQ ID NO:56), was isolated from the blood of a female patient exhibiting signs of immune deficiency. To do this, peripheral mononuclear cells (peripheral blood lymphocytes, PBL) and peripheral lymphocytes from the blood (PBL) of a donor who was not infected with HIV were stimulated with phytohemagglutinin and maintained in culture. For this purpose, use was made of the customary medium RPMI 1640 containing 10% fetal calf serum. The culture conditions are described in Landay A. et al., J. Inf. Dis., 161 (1990) pp. 706[\N]710. The formation of giant cells was then observed under the microscope. The production of HIV viruses was ascertained by determining the p 24 antigen using the test which can be purchased from Abbott. An additional test for determining the growth of the viruses consisted of the test using particle-bound reverse transcriptase (Eberle J., Seibl R., J. Virol. Methods 40, 1992, pp. 347–356). The growth of the viruses was therefore determined once or twice a week on the basis of the enzymatic activities in the culture supernatant, in order to monitor virus production. New donor lymphocytes were added once a week.

Once it was possible to observe HIV virus multiplication, fresh peripheral lymphocytes from the blood (PBL) of healthy donors, who were not infected with HIV, were infected with supernatant from the first culture. This step was repeated and the supernatant was then used to infect H 9 and HUT 78 cells. In this way, it was possible to achieve permanent production of the immunodeficiency virus. The virus was deposited with the ECACC under No. V 920 92 318.

EXAMPLE 2

So-called Western blot or immunoblot is currently a standard method for detecting HIV infections. Various sera were examined in accordance with the procedure described by GUrtler et al. in J. Virol. Meth. 15 (1987) pp. 11–23. In doing this, sera from German patients were compared with sera which had been obtained from African patients. The following results were obtained:

| Virus type | German sera | African sera |
|---|---|---|
| HIV-1, virus isolated from German patients | strong reaction | strong reaction using gp 41 |
| MVP-5180/91 (SEQ ID NO:56) | no reaction to weak reaction using gp 41 | strong reaction |

The results presented above demonstrate that a virus of the HIV-1 type isolated from German patients may possibly, if used for detecting HIV infections, fail to provide unambiguous results if the patient was infected with a virus corresponding to MVP-5180/91 (SEQ ID NO:56) according to the invention. It is assumed here that those viruses can be detected using the virus according to the invention which possess at least about 85% homology, based on the total genome, with the virus according to the invention.

EXAMPLE 3

Further Western blots were carried out in accordance with the procedure indicated in Example 2. The results are presented in the enclosed FIG. 3. In this test, the viral protein of the immunodeficiency virus MVP-5180/91 (SEQ ID NO:56) according to the invention, in the one case, and the viral protein of an HIV-1 type virus (MVP-899), in the other, was fractionated by gel electrophoresis and then transferred to cellulose filters. These filter strips were incubated with the sera from different patients and the specific antibodies were then rendered visible by a color reaction. The left half of the figure with the heading MVP-5180 shows the immunodeficiency virus according to the invention. The right half of the figure shows a virus (MVP-899), which is an HIV-1 virus, isolated from a German donor.

In FIG. 3, the same sera (from German patients) were in each case reacted with two respective filter strips, the numbers 8 and 26; 9 and 27; 10 and 28; 11 and 29; 12 and 30; 13 and 31; 14 and 32; 15 and 33, and 16 and 34 indicating the same sera. Sera from African patients were employed in the Western blots having the numbers 17 and 18. The numbers on the right hand margins indicate the approximate molecular weights in thousands (KD).

FIG. 3 shows clearly that sera from German patients only react very weakly with the immunodeficiency virus according to the invention in a Western blot using gp 41. By contrast, sera from African patients react very strongly with the immunodeficiency virus according to the invention. FIG. 3 makes it clear, therefore, that when the immunodeficiency virus according to the invention is used those immunodeficiency infections can be detected which only yield questionable, i.e. not unambiguously positive, results when an HIV-1 or HIV-2 virus is used. This option for detection can be of far-reaching diagnostic importance since, in those cases in which only questionable results are obtained in a Western blot, it cannot be established with unambiguous certainty whether an infection with an immunodeficiency virus is present. However, if the immunodeficiency virus according to the invention can be used to assign such questionable results to an infection with a virus of the type according to the invention, this then represents a substantial diagnostic advance.

EXAMPLE 4

DNA isolation, amplification and structural characterization of sections of the genome of the HIV isolate MVP-5180/91 (SEQ ID NO:56)

Genomic DNA from HUT 78 cells infected with MVP-5180/91 (SEQ ID NO:56) was isolated by standard methods.

In order to characterize regions of the genome of the isolate MVP-5180/91 (SEQ ID NO:56), PCR (polymerase chain reaction) experiments were carried out using a primer pair from the region of the coat protein gp 41. The PCR experiments were carried out in accordance with the method of Saiki et al. (Saiki et al., Science 239: 487–491, 1988) using the following modifications: for the amplification of regions of HIV-specific DNA, 5 μl of genomic DNA from HUT 78 cells infected with MVP-5180/91 were pipetted into a 100 μl reaction mixture (0.25 mM DNTP, in each case 1 μl primer 1 and primer 2, 10 mM Tris HCl, pH 8.3, 50 mM KCl, 1.5 mM $MgCl_2$, 0.001% gelatin, 2.5 units of Taq polymerase (Perkin Elmer)), and amplification was then carried out in accordance with the following temperature program: 1. initial denaturation: 3' 95° C., 2. amplification: 90" 94° C., 60" 56° C., 90" 72° C. (30 cycles).

The primers used for the PCR and for nucleotide sequencing were synthesized on a Biosearch 8750 oligonucleotide synthesizer. Primer 1 (SEQ ID NO:35): AGC AGC AGG AAG CAC TAT GG (coordinates from HIV-1 isolate HXB2: bases 7795–7814, corresponds to primer sk 68) (SEQ IN NO:21) Primer 2 (SEQ ID NO:36): GAG TTT TCC AGA GCA ACC CC (coordinates from HIV-1 isolate HXB2: bases 8003–8022, corresponds to primer env b (SEQ ID NO:20)

The amplified DNA was fractionated on a 3% "Nusievel" agarose gel (from Biozyme) and the amplified fragment was then cut out and an equal volume of buffer (1 * TBE (0.09M Tris borate, 0.002M EDTA, pH 8.0) was added to it. After incubating the DNA/agarose mixture at 70° C. for 10 minutes, and subsequently extracting with phenol, the DNA was precipitated from the aqueous phase by adding 1/10 vol of 3M NaAc, pH 5.5, and 2 vol of ethanol and storing at −20° C. for 15', and then subsequently pelleted in a centrifuge (Eppendorf) (13,000 rpm, 10', 4° C.). The pelleted DNA was dried and taken up in water, and then, after photometric determination of the DNA concentration at 260 nm in a spectrophotometer (Beckman), sequenced by the Sanger method (F. Sanger, Proc. Natl. Acad. Sci., 74: 5463, 1977). Instead of sequencing with Klenow DNA polymerase, the sequencing reaction was carried out using a kit from Applied Biosystems ("Taq aye deoxy terminator cycle sequencing", order No.: 401150). Primer 1 (SEQ ID NO:35) or primer 2 (SEQ ID NO:36) (in each case 1 μM) was employed as primers in separate sequencing reactions. The sequencing reaction was analysed on a 373A DNA sequencing apparatus (Applied Biosystems) in accordance with the instructions of the apparatus manufacturer.

The nucleotide sequence of the amplified DNA region, and the amino acid sequence deduced from it, are presented in Table 1. Table 1 includes the DNA sequences SEQ ID NO:37 and SEQ ID NO:38, as well as amino acid SEQ ID NO:39. The upper line in Table 1 corresponds to SEQ ID NO:37, the middle line corresponds to SEQ ID NO:38, and the third line corresponds to the amino acid SEQ ID NO:39.

TABLE 1

```
GCGCAGCGGCAACAGCGCTGACGGTACGGACCCACAGTGTACTGAAGGGTATAGTGCAAC
---------+---------+---------+---------+---------+---------+
CGCGTCGCCGTTGTCGCGACTGCCATGCCTGGGTGTCACATGACTTCCCATATCACGTTG

A   A   A   T   A   L   T   V   R   T   H   S   V   L   K   G   I   V   Q   Q

AGCAGGACAACCTGCTGAGAGCGATACAGGCCCAGCAACACTTGCTGAGGTTATCTGTAT
---------+---------+---------+---------+---------+---------+
TCGTCCTGTTGGACGACTCTCGCTATGTCCGGGTCGTTGTGAACGACTCCAATAGACATA

Q   D   N   L   L   R   A   I   Q   A   Q   Q   H   L   L   R   L   S   V   W

GGGGTATTAGACAACTCCGAGCTCGCCTGCAAGCCTTAGAAACCCTTATACAGAATCAGC
---------+---------+---------+---------+---------+---------+
CCCCATAATCTGTTGAGGCTCGAGCGGACGTTCGGAATCTTTGGGAATATGTCTTAGTCG

G   I   R   Q   L   R   A   R   L   Q   A   L   E   T   L   I   Q   N   Q   Q

AACGCCTAAACCTAT
---------+----- 195
TTGCGGATTTGGATA

R   L   N   L   -
```

EXAMPLE 5

The found nucleotide sequence from Table 1 was examined for homologous sequences in the GENEBANK database (Release 72, June 1992) using the GCG computer program (Genetic Computer Group, Inc., Wisconsin USA, Version 7.1, March 1992). Most of the nucleotide sequences of immunodeficient viruses of human origin and of isolates from primates known by July 1992 are contained in this database.

The highest homology shown by the nucleotide sequence from Table 1, of 66%, is to a chimpanzee isolate. The highest homology shown by the investigated DNA sequence from MVP-5180/91 (SEQ ID NO:56) to HIV-1 isolates is 64%. The DNA from Table 1 is 56% homologous to HIV-2 isolates. Apart from the chimpanzee isolate sequence, the best homology between the nucleotide sequence from Table 1 (SEQ ID NO:37; SEQ ID NO:38) and segments of DNA from primate isolates (SIV: simian immunodeficiency virus) is found with a DNA sequence encoding a part of the coat protein region from the SIV isolate (African long-tailed monkey) TYO-1. The homology is 61.5%.

EXAMPLE 6

The found amino acid sequence from Table 1 (SEQ ID NO:39) was examined for homologous sequences in the SWISSPROT protein database (Release 22, June 1992) using the GCG computer program. Most of the protein sequences of immunodeficiency viruses of human origin and of isolates from primates known by June 1992 are contained in this database.

The highest homology shown by the amino acid sequence from Table 1, (SEQ ID NO:39) of 62.5%, is to a segment of coat protein from the abovementioned chimpanzee isolate. The best homology among HIV-1 coat proteins to the amino acid sequence from Table 1 (SEQ ID NO:39) is found in the isolate HIV-1 Mal. The homology is 59%. The highest homology of the amino acid sequence from Table 1 (SEQ ID NO:39) to HIV-2 coat proteins is 52% (isolate HIV-2 Rod). Since HIV-1 and HIV-2 isolates, themselves, are at most only 64% identical in the corresponding protein segment, the MVP-5180/91 (SEQ ID NO:56) isolate appears to be an HIV variant which clearly differs structurally from HIV-1 and HIV-2 and thus represents an example of an independent group of HIV viruses.

The amino acid sequence of the amplified region of DNA (Table 1 (SEQ ID NO:39) from the HIV isolate MVP-5180/91 (SEQ ID NO:56) overlaps an immunodiagnostically important region of the coat protein gp 41 from HIV-1 (amino acids 584–618*) (Table 2 which includes SEQ ID NO:61 as the top line and SEQ ID NO:63 as the bottom line) (Gnann et al., J. Inf. Dis. 156: 261–267, 1987; Norrby et al., Nature, 329: 248–250, 1987).

Corresponding amino acid regions from the coat proteins of HIV-2 and SIV are likewise immunodiagnostically conserved (Gnann et al., Science, pp. 1346–1349, 1987). Thus, peptides from this coat protein region of HIV-1 and HIV-2 are employed as solid-phase antigens in many commercially available HIV-1/2 antibody screening tests. Approximately 99% of the anti-HIV-1 and anti-HIV-2 positive sera can be identified by them.

The amino acid region of the MVP-5180/91 coat protein (Table 1) could be of serodiagnostic importance owing to the overlap with the immunodiagnostically important region from gp 41. This would be the case particularly if antisera from HIV-infected patients failed to react positively with any of the commercially available antibody screening tests. In these cases, the infection could be with a virus which was closely related to MVP-5180/91 (SEQ ID NO:56).

TABLE 2

```
. . . . . . . . RI LAVERYLKDQQLLGI WGCSGKLICTTAVPWNAS
             ||  |:|  .:.:|||  |.:
         WGI RQLRARLQALETLI QNQQRLNL. . . . . . . . . . . . . . . . . .
```

EXAMPLE 7

DNA isolation, amplification and structural characterization of genome segments from the HIV isolate MVP-5180/91 (SEQ ID NO:56 encoding gp 41)

Genomic DNA from MVP-5180/91-infected HUT 78 cells was isolated as described.

In order to characterize genomic regions of the isolate MVP-5180/91 (SEQ ID NO:56, PCR (polymerase chain reaction) experiments were carried out using primer pairs from the gp 41 coat protein region. PCR (Saiki et al., Science 239: 487–491, 1988) and inverse PCR (Triglia et al., Nucl.

Acids, Res. 16: 8186, 1988) were carried out with the following modifications:

1. PCR

For the amplification of HIV-specific DNA regions, 5 μl (218 μg/ml) of genomic DNA from MVP-5180/91-infected HUT 78 cells were pipetted into a 100 μl reaction mixture (0.25 mM dNTP, in each case 1 μm primer 163env (SEQ ID NO:40) and primer envend (SEQ ID NO:41), 10 mM Tris HCl, pH 8.3, 50 mM KCl, 1.5 mM MgCl$_2$, 0.001% gelatin, 2.5 units of Taq polymerase (Perkin Elmer)), and amplification was then carried out in accordance with the following temperature program: 1. initial denaturation: 3 min. 95° C., 2. amplification: 90 sec. 94° C., 60 sec. 56° C., 90 sec. 72° C. (30 cycles).

2. Inverse PCR

The 5' region of gp 41 (N terminus) and the 3' sequence of gp 120 were amplified by means of "inverse PCR". For this, 100 μl of a genomic DNA preparation (218 μg/ml) from MVP-5180/91-infected HUT 78 cells were digested at 37° C. for 1 hour in a final volume of 200 μl using 10 units of the restriction endonuclease Sau3a. The DNA was subsequently extracted with phenol and then precipitated using sodium acetate (final concentration 300 mM) and 2.5 volumes of ethanol, with storage at -70° C. for 10 min, and then centrifuged down in an Eppendorf centrifuge; the pellet was then dried and resuspended in 890 μl of distilled water. Following addition of 100 μl of ligase buffer (50 mM Tris HCl, pH 7.8, 10 mM MgCl$_2$, 10 mM DTT, 1 mM ATP, 25 μg/ml bovine serum albumin) and 10 μl of T4 DNA ligase (from Boehringer, Mannheim), the DNA fragments were ligated at room temperature for 3 hours and then extracted with phenol once again and precipitated with sodium acetate and ethanol as above. After centrifuging, down and drying, the DNA was resuspended in 40 μl of distilled water and digested for 1 hour with 10 units of the restriction endonuclease SacI (from Boehringer, Mannheim). 5 μl of this mixture were then employed in a PCR experiment as described under "1. PCR". The primers 168i (SEQ ID NO:42) and 169i (SEQ ID NO:43) were used for the inverse PCR in place of primers 163env (SEQ ID NO:40) and envend (SEQ ID NO:41).

The primers 163env (SEQ ID NO:40), 168i (SEQ ID NO:42) and 169i (SEQ ID NO:43) were selected from that part of the sequence of the HIV isolate MVP-5180 (SEQ ID NO:56) which had already been elucidated (Example 4).

The primers used for the PCR/inverse PCR and the nucleotide sequencing were synthesized on a Biosearch 8750 oligonucleotide synthesizer, with the primers having the following sequences:

Primer 163env (SEQ ID NO:40): 5' CAG AAT CAG CAA CGC CTA AAC C 3'

Primer envend (SEQ ID NO:41) : 5' GCC CTG TCT TAT TCT TCT AGG 3' (position from HIV-1 isolate BH10: bases 8129–8109)

Primer 168i (SEQ ID NO:42): 5' GCC TGC AAG CCT TAG AAA CC 3'

Primer 169i (SEQ ID NO:43): 5' GCA CTA TAC CCT TCA GTA CAC TG 3'

The amplified DNA was fractionated on a 3% "Nusieve" agarose gel (from Biozyme) and the amplified fragment was then cut out and an equal volume of buffer (1 * TBE (0.09M Tris borate, 0.002M EDTA, pH 8.0)) was added to it. After incubating the DNA/agarose mixture at 70° C. for 10 minutes, and subsequent phenol extraction, the DNA was precipitated from the aqueous phase by adding ⅒ vol of 3M NaAc, pH 5.5, and 2 vol of ethanol, and storing at -20° C. for 15', and then pelleted in an Eppendorf centrifuge (13,000 rpm, 10 ', 4° C.). The pelleted DNA was dried and then taken up in water and sequenced by the method of Sanger (F. Sanger, Proc. Natl. Acad. Sci., 74: 5463, 1977) following photometric determination of the DNA concentration at 260 nm in a spectrophotometer (from Beckman). Instead of sequencing with Klenow DNA polymerase, the sequencing reaction was carried out using a kit from Applied Biosystems ("Taq dye deoxy terminator cycle sequencing", order No.: 401150). Primer 163env (SEQ ID NO:40) or primer envend (SEQ ID NO:41)(in each case 1 μM) was employed as the primer in separate sequencing reactions. The amplified DNA from the inverse PCR experiment was sequenced using primers 168i (SEQ ID NO:42) and 169i (SEQ ID NO:43). The sequencing reaction was analysed on an Applied Biosystems 373A DNA sequencing apparatus in accordance with the instructions of the apparatus manufacturer.

The nucleotide sequence of the amplified DNA region, and the amino acid sequence deduced from it, are presented in Table 3. Table 3 includes DNA sequences SEQ ID NO:44 and SEQ ID NO:45, as well as amino acid sequences SEQ ID NO:46. In Table 3, the top line corresponds to SEQ ID NO:44, the middle line corresponds to SEQ ID NO:45, and the third line represents amino acid sequence SEQ ID NO:46.

TABLE 3

```
    AAATGTCAAGACCAATAATAAACATTCACACCCCTCACAGGGAAAAAAGAGCAGTAGGAT
1   ---------+---------+---------+---------+---------+---------+   60
    TTTACAGTTCTGGTTATTATTTGTAAGTGTGGGGAGTGTCCCTTTTTTCTCGTCATCCTA

M   S   R   P   I   I   N   I   H   T   P   H   R   E   K   R | A   V   G   L
                                                                gp120 ←――――|――――→ gp41

TGGGAATGCTATTCTTGGGGGTGCTAAGTGCAGCAGGTAGCACTATGGGCGCAGCGGCAA
61  ---------+---------+---------+---------+---------+---------+   120
    ACCCTTACGATAAGAACCCCCACGATTCACGTCGTCCATCGTGATACCCGCGTCGCCGTT

G   M   L   F   L   G   V   L   S   A   A   G   S   T   M   G   A   A   A   T

CAGCGCTGACGGTACGGACCCACAGTGTACTGAAGGGTATAGTGCAACAGCAGGACAACC
121 ---------+---------+---------+---------+---------+---------+   180
    GTCGCGACTGCCATGCCTGGGTGTCACATGACTTCCCATATCACGTTGTCGTCCTGTTGG

A   L   T   V   R   T   H   S   V   L   K   G   I   V   Q   Q   Q   D   N   L
```

TABLE 3-continued

```
    TGCTGAGAGCGATACAGGCCCAGCAACACTTGCTGAGGTTATCTGTATGGGGTATTAGAC
181 ---------+---------+---------+---------+---------+---------+ 240
    ACGACTCTCGCTATGTCCGGGTCGTTGTGAACGACTCCAATAGACATACCCCATAATCTG

L   R   A   I   Q   A   Q   Q   H   L   L   R   L   S   V   W   G   I   R   Q

AACTCCGAGCTCGCCTGCAAGCCTTAGAAACCCTTATACAGAATCAGCAACGCCTAAACC
241 ---------+---------+---------+---------+---------+---------+ 300
    TTGAGGCTCGAGCGGACGTTCGGAATCTTTGGGAATATGTCTTAGTCGTTGCGGATTTGG

L   R   A   R   L   Q   A   L   E   T   L   I   Q   N   Q   Q   R   L   N   L

TATGGGGCTGTAAAGGAAAACTAATCTGTTACACATCAGTAAAATGGAACACATCATGGT
301 ---------+---------+---------+---------+---------+---------+ 360
    ATACCCCGACATTTCCTTTTGATTAGACAATGTGTAGTCATTTTACCTTGTGTAGTACCA

W   G   C   K   G   K   L   I   C   Y   T   S   V   K   W   N   T   S   W   S

CAGGAGGATATAATGATGACAGTATTTGGGACAACCTTACATGGCAGCAATGGGACCAAC
361 ---------+---------+---------+---------+---------+---------+ 420
    GTCCTCCTATATTACTACTGTCATAAACCCTGTTGGAATGTACCGTCGTTACCCTGGTTG

G   G   Y   N   D   D   S   I   W   D   N   L   T   W   Q   Q   W   D   Q   H

ACATAAACAATGTAAGCTCCATTATATATGATGAAATACAAGCAGCACAAGACCAACAGG
421 ---------+---------+---------+---------+---------+---------+ 480
    TGTATTTGTTACATTCGAGGTAATATATACTACTTTATGTTCGTCGTGTTCTGGTTGTCC

I   N   N   V   S   S   I   I   Y   D   E   I   Q   A   A   Q   D   Q   Q   E

AAAAGAATGTAAAAGCATTGTTGGAGCTAGATGAATGGGCCTCTCTTTGGAATTGGTTTG
481 ---------+---------+---------+---------+---------+---------+ 540
    TTTTCTTACATTTTCGTAACAACCTCGATCTACTTACCCGGAGAGAAACCTTAACCAAAC

K   N   V   K   A   L   L   E   L   D   E   W   A   S   L   W   N   W   F   D

ACATAACTAAATGGTTGTGGTATATAAAAATAGCTATAATCATAGTGGGAGCACTAATAG
541 ---------+---------+---------+---------+---------+---------+ 600
    TGTATTGATTTACCAACACCATATATTTTTATCGATATTAGTATCACCCTCGTGATTATC

I   T   K   W   L   W   Y   I   K   I   A   I   I   I   V   G   A   L   I   G

GTATAAGAGTTATCATGATAGTACTTAATCTAGTGAAGAACATTAGGCAGGGATATCAAC
601 ---------+---------+---------+---------+---------+---------+ 660
    CATATTCTCAATAGTACTATCATGAATTAGATCACTTCTTGTAATCCGTCCCTATAGTTG

I   R   V   I   M   I   V   L   N   L   V   K   N   I   R   Q   G   Y   Q   P

CCCTCTCGTTGCAGATCCCTGTCCCACACCGGCAGGAAGCAGAAACGCCAGGAAGAACAG
661 ---------+---------+---------+---------+---------+---------+ 720
    GGGAGAGCAACGTCTAGGGACAGGGTGTGGCCGTCCTTCGTCTTTGCGGTCCTTCTTGTC

L   S   L   Q   I   P   V   P   H   R   Q   E   A   E   T   P   G   R   T   G

GAGAAGAAGGTGGAGAAGGAGACAGGCCCAAGTGGACAGCCTTGCCACCAGGATTCTTGC
721 ---------+---------+---------+---------+---------+---------+ 780
    CTCTTCTTCCACCTCTTCCTCTGTCCGGGTTCACCTGTCGGAACGGTGGTCCTAAGAACG

E   E   G   G   E   G   D   R   P   K   W   T   A   L   P   P   G   F   L   Q

AACAGTTGTACACGGATCTCAGGACAATAATCTTGTGGACTTACCACCTCTTGAGCAACT
781 ---------+---------+---------+---------+---------+---------+ 840
    TTGTCAACATGTGCCTAGAGTCCTGTTATTAGAACACCTGAATGGTGGAGAACTCGTTGA

Q   L   Y   T   D   L   R   T   I   I   L   W   T   Y   H   L   L   S   N   L

TAATATCAGGGATCCGGAGGCTGATCGACTACCTGGGACTGGGACTGTGGATCCTGGGAC
841 ---------+---------+---------+---------+---------+---------+ 900
    ATTATAGTCCCTAGGCCTCCGACTAGCTGATGGACCCTGACCCTGACACCTAGGACCCTG

I   SG  I   R   R   L   I   D   Y   L   G   L   G   L   W   I   L   G   Q

AAAAGACAATTGAAGCTTGTAGACTTTGTGGAGCTGTAATGCAATATTGGCTACAAGAAT
901 ---------+---------+---------+---------+---------+---------+ 960
    TTTTCTGTTAACTTCGAACATCTGAAACACCTCGACATTACGTTATAACCGATGTTCTTA

K   T   I   E   A   C   R   L   C   G   A   V   M   Q   Y   W   L   Q   E   L
```

TABLE 3-continued

```
    TGAAAAATAGTGCTACAAACCTGCTTGATACTATTGCAGTGTCAGTTGCCAATTGGACTG
961 ---------+---------+---------+---------+---------+---------+ 1020
    ACTTTTTATCACGATGTTTGGACGAACTATGATAACGTCACAGTCAACGGTTAACCTGAC

K  N  S  A  T  N  L  L  D  T  I  A  V  S  V  A  N  W  T  D

ACGGCATCATCTTAGGTCTACAAAGAATAGGACAAGG
1021 ---------+---------+---------+-------  1057
     TGCCGTAGTAGAATCCAGATGTTTCTTATCCTGTTCC

G  I  I  L  G  L  Q  R  I  G  Q
```

EXAMPLE 8

The found nucleotide sequence from Table 3 (SEQ ID NO:44;SEQ ID NO:46) was examined for homologous sequences in the GENEBANK database (Release 72, June 1992) using the GCG computer program (Genetic Computer Group, Inc. Wisconsin USA, version 7.1, March 1992). Most of the nucleotide sequences of immunodeficiency viruses of human origin and of isolates from primates known by July 1992 are contained in this database.

The highest homology of the nucleotide sequence from Table 3 (SEQ ID NO:44; SEQ ID NO:45) to an HIV-1 isolate is 62%. The DNA from Table 5 is 50% homologous to HIV-2 isolates.

The amino acid sequence deduced from the nucleotide sequence from Table 3 (SEQ ID NO:46) was examined for homologous sequences in the SWISSPROT protein database (Release 22, June 1992) using the GCG computer program. Most of the protein sequences of immunodeficiency viruses of human origin and of isolates from primates known by June 1992 are contained in this database.

At best, the amino acid sequence from Table 3 (SEQ ID NO:46) is 54% homologous to the corresponding coat protein segment from a chimpanzee isolate CIV (SIVcpz) and 54.5% homologous to the HIV-1 isolate Mal. At best, the amino acid sequence from Table 3 (SEQ ID NO:46) is 34% homologous to HIV-2 coat proteins (isolate HIV-2 D194).

If, by contrast, the gp 41 amino acid sequence of HIV-1 is compared with the HIV-1 gp 41 sequence present in the SWISSPROT database, the highest homology is, as expected, almost 100%, and the lowest 78%.

These clear structural differences between the sequence region from Table 3 and the corresponding segment from HIV-1 and HIV-2 suggest that isolate MVP-5180/91 (SEQ ID NO:56) is an HIV variant which clearly differs structurally from HIV-1 and HIV-2. It is possible that MVP-5180/91 (SEQ ID NO:56) should be assigned to a separate group of HIV viruses which differ from HIV-1 and HIV-2.

The peptide from amino acid 584 to amino acid 618 of the HIV-1 coat protein region is of particular serodiagnostic interest (SEQ ID NO:61) (numbering in accordance with Wain Hobson et al., Cell 40: 9–17, 1985; Gnann et al., J. Inf. Dis. 156: 261–267, 1987; Norrby et al., Nature, 329: 248–250, 1987). Corresponding amino acid regions from the coat proteins of HIV-2 and SIV are likewise immunodiagnostically conserved (Gnann et al., Science, pp. 1346–1349, 1987). Thus, peptides from this coat protein region of HIV-1 and HIV-2 are employed as solid-phase antigens in many commercially available HIV-1/2 antibody screening tests. Using them, approximately 99% of the anti-HIV-1 and anti-HIV-2 positive sera can be identified.

The corresponding amino acid region of the MVP-5180/91 coat protein (Table 4), as well as the whole gp 41 of this isolate, could be of serodiagnostic importance, particularly if antisera from HIV-infected patients either did not react at all or only reacted weakly in commercially available antibody screening tests. In these cases, the infection could be due to a virus which is closely related to MVP-5180/91 (SEQ ID NO:56). Table 4 includes SEQ ID NO:61 which is designated as line 1, and also highlights in line 2 the points of difference from the amino acid sequence designated SEQ ID NO:62. Amino acid sequence SEQ ID NO:62 appears in full following Table 4.

TABLE 4

```
1  RI LAVERYL KDQQLLGI WGCS GKLI CTTAVP WNAS
2     LQ  L  TLI QN    R  NL    K        Y S K    T
```

1  HIV-1 amino acid sequence from gp 41 (SEQ ID NO: 61)
2  MVP-5180 sequence from gp 41. Only differences from the HIV-1 sequence are indicated.

The peptide, which was found with the aid of information deriving from MVP-5180, thus has the amino acid sequence (SEQ ID NO:62): RLQALETLIQNQQRLNLWGCKGKLI-CYTSVKWNTS.

The present invention therefore relates to peptides which can be prepared recombinantly or synthetically and have the sequence indicated above, or a constituent sequence thereof, the constituent sequences having at least 6 consecutive amino acids, preferably 9 and particularly preferably 12 consecutive amino acids.

EXAMPLE 9

Cloning of the whole genome of the HIV isolate MVP-5180 (SEQ ID NO:56)

a) Preparation of a genomic library

Genomic DNA from MVP-5180-infected HUT 78 cells was isolated as described. 300 µg of this DNA were incubated for 45 min in a volume of 770 µl together with 0.24 U of the restriction enzyme Sau3A. The DNA, which was only partially cut in this incubation, was subsequently size-fractionated on a 0.7% agarose gel (low melting agarose, Nusieve) and fragments of between 10 and 21 kb were cut out. The agarose was melted at 70° C. for 10 min and the same volume of buffer (1 * TBE, 0.2 M NaCl) was then added to it. Subsequently, after having extracted twice with phenol and once with chloroform, the DNA was precipitated by adding 1/10 vol. of 3M sodium acetate solution (pH 5.9) and 2.5 vol. of ethanol, and storing at −70° C. for 10 min. The precipitated DNA was centrifuged down and dried and then dissolved in water at a concentration of 1 µg/µl. The yield of size-fractionated DNA was about 60 µg. 5 µg of this DNA were incubated at 37° C. for 20 min in an appropriate buffer together with 1 U of alkaline phosphatase. In this way, the risk of multiple insertions of size-fractionated DNA was reduced by eliminating the 5'-terminal phosphate radical. The phosphatase treatment was stopped by extracting with phenol and the DNA was precipitated as above and then ligated at 15° C. for 12 hours together with 1 μg of the vector (2 DASH, BamHI-cut, Stratagene No.: 247611) in a total volume of 6 μl using 2 Weiss units of Lambda T4 ligase. Following completed ligation, the DNA was packaged into phage coats using a packaging kit (Gigapack II Gold, Stratagene No.: 247611) precisely in accordance with the manufacture's instructions.

b) Radioactive labeling of the DNA probe

The "random-primed DNA labeling kit" from Boehringer Mannheim (No.: 713 023) was employed for the labeling. The PCR product was labeled which was obtained as described in Example 3 using the primers sk68 (SEQ ID NO:21) and envb. (SEQ ID NO:20) 1 μg of this DNA was denatured by 2 * 5 min of boiling and subsequent cooling in ice water. 50 mCi [a-$^{32}$p]-dCTP (NEN, No.: NEX-053H) were added for the labeling. Other ingredients were added by pipette in accordance with the manufacturer's instructions. Following a 30 min incubation at 37° C., the DNA, which was now radioactively labeled, was precipitated.

c) Screening the phage library 20,000 pfu (plaque-forming units) of the library in 100 μl of SM buffer (5.8 g of NaCl, 2 g of MgSO$_4$, 50 ml of 1M Tris, pH 7.5, and 5 ml of a 2% gelatin solution, dissolved in 1 l of H$_2$O) were added to 200 μl of a culture (strain SRB(P2) [Stratagene, No.: 247611] in LB medium, which contained 10 mM MgSO$_4$ and 0.2% maltose) which had been grown at 30° C. overnight; the phages were adsorbed to the bacteria at 37° C. for 20 min and 7.5 ml of top agarose, which had been cooled to 55° C., was then mixed in and the whole sample was distributed on a pre-warmed LB agar plate of 14 cm diameter. The plaques achieved confluence after about 8 hours. After that, nitrocellulose filters were laid on the plates for a few minutes and were marked asymmetrically. After having been carefully lifted from the plates, the filters were denatured for 2 min (0.5M NaOH, 1.5M NaCl) and then neutralized for 5 min (0.5M Tris, pH 8, 1.5M NaCl). The filters were subsequently baked at 80° C. for 60 min and could then be hybridized to the probe. For the prehybridization, the filters were incubated at 42° C. for 2–3 h, while shaking, in 15 ml of hybridization solution (50% formamide, 0.5% SDS, 5 * SSPE, 5 * Denhardt's solution and 0.1 mg/ml salmon sperm DNA) per filter. The [$^{32}$P]-labeled DNA probes were denatured at 100° C. for 2–5 min and then cooled on ice; they were then added to the prehybridization solution and hybridization was carried out at 42° C. for 12 hours. Subsequently, the filters were washed at 60° C., firstly with 2 * SSC/0.1% SDS and then with 0.2 * SSC/0.1% SDS. After the filters had been dried, hybridization signals were detected using the X-ray film X-OMAT™AR (Kodak).

Following elution in SM buffer, those plaques to which it was possible to assign a signal were individually separated in further dilution steps. It was possible to identify the clone described below following screening of 2 * 10$^6$ plaques.

d) Isolation of the phage DNA and subcloning

An overnight culture of the host strain SRB (P2) was infected with 10 11 of a phage eluate in SM buffer such that the culture initially grew densely but then lysed after about 6–8 h. Cell remnants were separated off from the lysed culture by centrifuging it twice at 9,000 g for 10 min. Subsequently, the phage were pelleted by centrifugation (35,000 g, 1 h), and then taken up in 700 μl of 10 mM MgSO$_4$ and extracted with phenol until a protein interface could no longer be seen. The phage DNA was then precipitated and cleaved with the restriction enzyme EcoRI, and the resulting EcoRI fragments were subcloned into the vector Bluescript KS$^-$(Stratagene, No.: 212208). In all, 4 clones were obtained:

| Plasmid | Beginning[1] | End[1] |
|---|---|---|
| pSP1 | 1 | 1785 |
| pSP2 | 1786 | 5833 |
| pSP3 | 5834 | 7415 |
| pSP4 | 7660 | 9793 |

[1]refers to the total sequence below

The missing section between bases 7416 and 7659 was obtained by PCR using the primers 157 (CCA TAA TAT TCA GCA GAA CTA G) and 226 (GCT GAT TCT GTA TAA GGG). The phage DNA of the clone was used as the DNA template. The conditions for the PCR were: 1.) initial denaturation: 94° C., 3 min, 2.) amplification: 1.5 min 94° C., 1 min 56° C. and 1 min 72° C. for 30 cycles. The DNA was sequenced as described in Example 4. Both the strand and the antistrand of the total genome were sequenced. In the case of each site for EcoRI cleavage, PCR employing phage DNA of the clone as the DNA template was used to verify that there was indeed only the one EcoRI cleavage site at each subclone transition point.

TABLE 5

The position of the genes for the virus proteins GAG, POL and ENV in the full sequence of MVP-5180

| Gene | Start[1] | Stop[1] |
|---|---|---|
| GAG | 817 | 2310 |
| POL | 2073 | 5153 |
| ENV | 6260 | 8887 |

[1]The numbers give the positions of the bases in the full sequence of MVP-5180/91 (SEQ ID NO:56). The full sequence of MVP-5180/91 is presented in FIG. 4 (SEQ ID NO:56).

EXAMPLE 10

Delimitation of the full sequence of MVP-5180/91 (SEQ ID NO:56) from other HIV-1 isolates The databanks Genbank, Release 75 of 2.93, EMBL 33 of 12.92, and Swissprot 24 of 1.93 provided the basis for the following sequence comparisons. Comparisons of homology were carried out using the GCG software (version 7.2, 10.92. from the Genetics Computer Group, Wisconsin).

Initially, the sequences of GAG, POL and ENV were compared with the database at the amino acid level using the "Wordsearch" program. The 50 best homologs were in each case compared with each other using the "Pileup" program. From this, it clearly emerges that MVP-5180/91 (SEQ ID NO:56) belongs in the HIV-1 genealogical tree but branches off from it at a very early stage, even prior to the chimpanzee virus SIVcpz, and thus represents a novel HIV-1 subfamily. In order to obtain numerical values for the homologies, MVP-5180 (SEQ ID NO:56) was compared with the HIV-1, HIV-2 and SIV sequences which in each case showed the best fit, and in addition with the SIVcpz sequence, using the "Gap" program.

TABLE 6

Homology values for the amino acid sequences of
GAG, POL and ENV of the MVP-5180/91 isolate

| GAG | SIVcpz | 70.2%<br>83.6% | HIV1u[2] | 69.9%<br>81.2% | HIV2d[3] | 53.6%<br>71.3% | SIV1a[4] | 55.1%<br>71.3% |
|---|---|---|---|---|---|---|---|---|
| POL | SIVcpz | 78.0%<br>88.0% | HIV1u[2] | 76.1%<br>86.8% | HIV2d[3] | 57.2%<br>71.9% | SIVgb[5] | 57.7%<br>74.6% |
| ENV | SIVcpz | 53.4%<br>67.1% | HIV1h[1] | 50.9%<br>67.2% | HIV2d[3] | 34.4%<br>58.7% | SIVat[6] | 34.4%<br>57.8% |

[1]h = hz321/Zaire, [2]u = u455/Uganda, [3]d = jrcst, [4]a = agm155, [5]gb = gb1, [6]at = agm The upper numerical value expresses the identity and the lower value the similarity of the two sequences. In addition to this, the database was searched at the nucleotide level using "Wordsearch" and "Gap". The homology values for the best matches in each case are compiled in Table 7.

TABLE 7

Homology values for the nucleotide sequence of
MVP-5180/91

|  | HIV1 |  | HIV2 |  |
|---|---|---|---|---|
| gag | HIVelicg | 70.24% | HIV2bihz | 60.0% |
| pol | HIVmal | 75.0% | HIV2cam2 | 62.9% |
| env | HIVsimi84 | 59.7% | HIV2gha | 49.8% |

EXAMPLE 11

Description of the PCR amplification, cloning and seauencing of the gag gene of the HIV 5180 isolate In order to depict the spontaneous mutations arising during the course of virus multiplication, a part of the viral genome was cloned using the PCR technique and the DNA sequence thus obtained was compared with the sequence according to FIG. 4 (SEQ ID NO:56).

Figure 5:
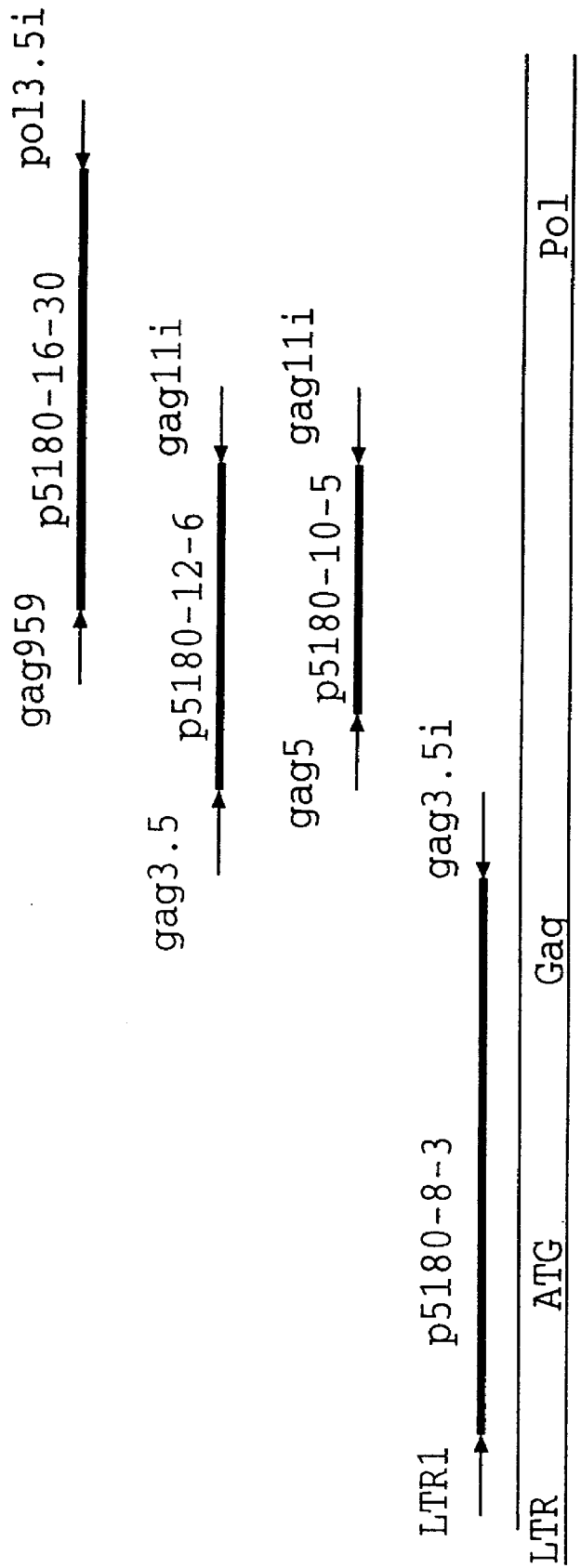
FIG. 5 depicts the strategy for PCR amplification, cloning, and sequencing of MVP-5180/91.
Figure 8:
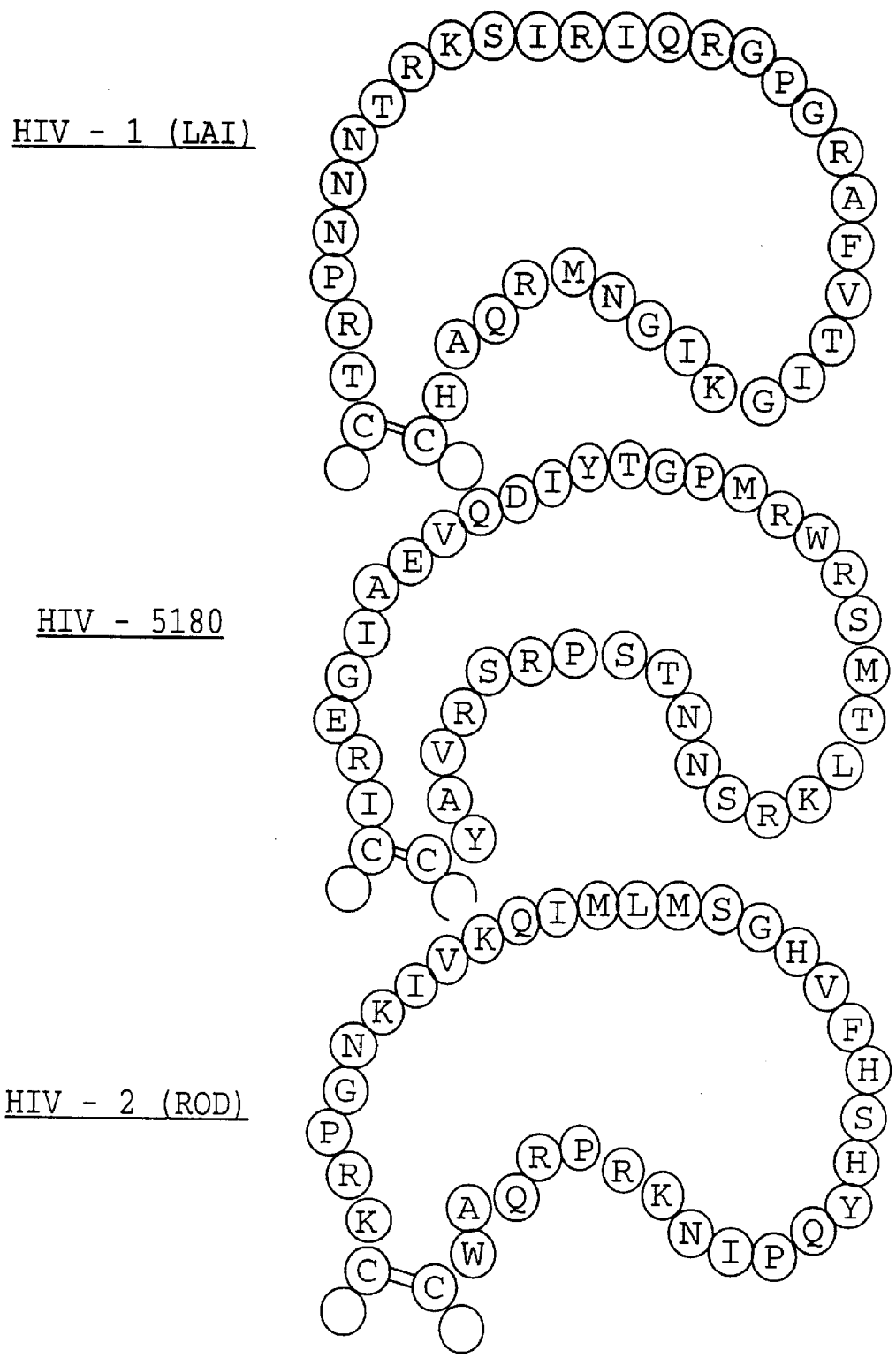
FIG. 8 depicts the immunological specificities of the V3 loop of HIV-1, HIV-2, and MVP-5180/91.

The gag sequence was cloned in an overlapping manner from the LTR (long terminal repeat, LTR1 primer) of the left end of the MVP-5180 genome through into the pol gene (polymerase gene, pol3.5i primer). The cloning strategy is depicted schematically in FIG. 5. The PCR reactions were carried out using the DNA primers given below, whose sequences were derived from the HIV-1 consensus sequence. The sequencings were carried out using the dideoxy chain termination method. The sequence encoding the MVP-5180 gag gene extends from nucleotide 817 (A of the ATG start codon) to nucleotide 2300 (A of the last codon).

LTR1:
5'- CTA GCA GTG GCG CCC GAA CAG G -3' gag3.5:
5'- AAT GAG GAA GCU GCA GAU TGG GA -3'
(U = A/T)

gag 3.5i:
5'- TCC CAU TCT GCU GCT TCC TCA TT -3'
(U = A/T)

gag5:
5'- CCA AGG GGA AGT GAC ATA GCA GGA AC -3' gag959:
5'- CGT TGT TCA GAA TTC AAA CCC -3' gag11i:
5'- TCC CTA AAA AAT TAG CCT GTC -3' pol3.5i:
5'- AAA CCT CCA ATT CCC CCT A -3'

The DNA sequence obtained using thee PCR technique was compared with the DNA sequence presented in FIG. 4 (SEQ ID NO:56). A comparison of the two DNA sequences is presented in FIG. 6. FIG. 6 includes SEQ ID NO:57, which corresponds to FIG. 4 (SEQ ID NO:56) and SEQ ID NO:58 which corresponds to the DNA sequence obtained using the PCR technique. This showed that about 2% of the nucleotides differ from each other, although the virus is the same in the two cases. In FIG. 6, the upper line in each case represents the DNA sequence which is presented in FIG. 4 (SEQ ID NO:56) and the lower line represents the DNA sequence obtained using the PCR technique.

In addition, the amino acid sequence of the gag protein, elucidated using the PCR technique, was compared with the amino acid sequence of the corresponding protein deduced from FIG. 4. This showed an amino acid difference of about 2.2%. The comparison is presented in FIG. 7, the lower line in each case representing the amino acid sequence which was deduced from the sequence obtained using the PCR technique. FIG. 7 includes amino acid SEQ ID NO:59, which was elucidated in accordance with FIG. 4 (SEQ ID NO:56), and the amino acid sequence derived using the PCR technique which is SEQ ID NO:60.

EXAMPLE 12

The sequence of the virus MVP-5180 (SEQ ID NO:56) according to the invention was compared with the consensus sequences of HIV-1 and HIV-2, and with the sequence of ANT-70 (WO 89/12094), insofar as this was known.

In this connection, the following results were obtained:

TABLE 8

| Gene locus | Deviating nucleotides | Number of the nucleotides | % homology (approximated) |
|---|---|---|---|
| LTR | 207 | 630 | HIV-1 67% |
|  | 308 |  | HIV-2 51% |
|  | 115 |  | ANT 70 82% |
| GAG | 448 | 1501 | HIV-1 70% |
|  | 570 |  | HIV-2 62% |
| POL | 763 | 3010 | HIV-1 74% |
|  | 1011 |  | HIV-2 66% |
| VIF | 183 | 578 | HIV-1 68% |
|  | 338 |  | HIV-2 42% |
| ENV | 1196 | 2534 | HIV-1 53% |
|  | 1289 |  | HIV-2 49% |
| NEF | 285 | 621 | HIV-1 54% |
|  | 342 |  | HIV-2 45% |
| total | 3082 | 8874 | HIV-1 65% |
|  | 3858 |  | HIV-2 56% |

In the above table, "HIV-1" denotes consensus sequences of HIV-1 viruses; "HIV-2" denotes consensus sequences of HIV-2 viruses; ANT-70 denotes the partial sequence of a virus designated HIV-3 and disclosed in WO 89/12094.

The present invention therefore relates to viruses, DNA sequences and amino acid sequences, and constituent sequences thereof, which possess such a degree of homology with the sequence presented in FIG. 4 (SEQ ID NO:56), based on the gene loci, that at most the fractions given in Table 9, expressed in % values, are different.

TABLE 9

Homology based on gene loci, expressed as maximum differences

| Gene locus | Differences | Preferred differences | Particularly preferred differences |
|---|---|---|---|
| LTR | 17% | 15% | 10% |
| GAG | 29% | 28% | 14% |
| POL | 25% | 24% | 12% |
| VIF | 31% | 30% | 15% |
| ENV | 46% | 45% | 22% |
| NEF | 16% | 12% | 10% |

The homology values in % given in Table 9 mean that, when comparing the sequence according to FIG. 4 (SEQ ID NO:56) with a sequence of another virus, at most a fraction of the sequence corresponding to the abovementioned percentage values may be different.

EXAMPLE 13

V3 loop

This loop is the main neutralizing region in HIV and the immunological specificities of the region are documented in summary form in FIG. 8. This is a copy from a work by Peter Nara (1990) from AIDS. The amino acid sequence of the V3 loop is shown diagrammatically and is compared with the IIIB virus, now LAI, and the first HIV-2 isolate (ROD). Individual amino acids are conserved at the cystine bridge. Whereas the crown of HIV-1 is GPGR or GPGQ and that of HIV-2 is GHVF, the crown of MVP-5180/91 (SEQ ID NO:56) is formed from the amino acids GPMR. The motif with methionine has not previously been described and emphasizes the individuality of MVP-5180/91 (SEQ ID NO:56).

After having determined the nucleotide sequence of the virus the V3-loop-region was amplified using the PCR-technique by using suitable primers. Some mutations have been observed, especially a change of the methionine codon (ATG) to the leucine codon (CTG).

In the following the amino acid sequence derived from the cloned nucleic acid is compared with a sequence obtained after amplification with the help of PCR technology MvP 5180 (cloned) (SEQ ID NO:54):
C I R E G I A E V Q D I Y T G P M R - WRSMTLKRSNNTSPRSRVAYC
MvP 5180 (PCT technique) (SEQ ID NO:55):
C I R E G I A E V Q D L H T G P L R - WRSMTLKKSSNSHTQPRSKVAYC

EXAMPLE 14

In order to demonstrate that even those sera which cannot be identified in a normal HIV-1+2 screening test can be proved to be HIV-1-positive with the aid of the virus MVP-5180 (SEQ ID NO:56) according to the invention, or antigens derived therefrom, various sera from patients from the Cameroons were examined in the EIA test.

156 anti-HIV-1-positive sera were examined in a study carried out in the Cameroons. Substantial, diagnostically relevant differences were observed in two of these sera. The extinctions which were measured are given in Table 10 below. CAM-A and CAM-B denote the sera of different patients.

TABLE 10

| Patient sera | MVP-5180-EIA | HIV-1 + HIV-2 EIA |
|---|---|---|
| CAM-A | 2.886 | 1.623 |
| CAM-B | 1.102 | 0.386 |

The cutoff for both tests was 0.300.

In a further study on 47 anti-HIV-1-positive sera from the Cameroons, two sera were of particular note. One of these (93–1000) derives from a patient showing relatively few symptoms and the other (93–1001) from a patient suffering from AIDS. The extinction values for the two EIA tests are compared in Table 11 below:

TABLE 11

| Patient sera | MVP-5180-EIA | HIV-1 + HIV-2 EIA |
|---|---|---|
| 93-1000 | >2.5 | 1.495 |
| 93-1001 | 0.692 | 0.314 |

The cutoff was 0.3 in this case as well. The extinction values for patient 93–1001 demonstrate that the normal HIV-1+HIV-2 EIA can fail whereas clear detection is possible if the antigen according to the invention is employed.

We claim:

1. A cDNA which is complementary to the RNA, or parts of said RNA which encode at least 15 amino acids, of an immunodeficiency virus having all the morphological and immunological properties of retrovirus MVP-5180/91 (SEQ ID NO:56) which has been deposited with the European Collection of Animal Cell Culture (ECACC) under No. V 920 92 318, and having a sequence homology of more than 70% to the env gene of the retrovirus MVP-5180/91.

2. A cDNA which is complementary to the RNA, or parts of said RNA which encode at least 15 amino acids, of the immunodeficiency virus MVP-5180/91 (SEQ ID NO:56) deposited with the European Collection of Animal Cell Cultures (ECACC) under NO. V 920 92 318.

* * * * *